US 10,213,288 B2

(12) United States Patent
Johnson et al.

(10) Patent No.: US 10,213,288 B2
(45) Date of Patent: Feb. 26, 2019

(54) DISTAL PROTECTION FILTER

(75) Inventors: Eric Johnson, Woodside, CA (US);
Gilbert Laroya, Santa Clara, CA (US);
Paul Do, San Jose, CA (US)

(73) Assignee: CRUX BIOMEDICAL, INC., Menlo Park, CA (US)

( * ) Notice: Subject to any disclaimer, the term of this patent is extended or adjusted under 35 U.S.C. 154(b) by 1057 days.

(21) Appl. No.: 13/472,417

(22) Filed: May 15, 2012

(65) Prior Publication Data

US 2013/0238010 A1 Sep. 12, 2013

Related U.S. Application Data

(60) Provisional application No. 61/607,191, filed on Mar. 6, 2012.

(51) Int. Cl.
*A61F 2/01* (2006.01)
*A61B 17/221* (2006.01)
*A61B 17/00* (2006.01)
*A61M 29/00* (2006.01)

(52) U.S. Cl.
CPC ........ *A61F 2/013* (2013.01); *A61F 2002/015* (2013.01); *A61F 2250/0008* (2013.01)

(58) Field of Classification Search
CPC .............. A61F 2/013; A61F 2250/0008; A61F 2002/015
See application file for complete search history.

(56) References Cited

U.S. PATENT DOCUMENTS

| 152,652 A | 6/1874 | Knowlton |
|---|---|---|
| 407,971 A | 7/1889 | Siersdorfer |
| 621,937 A | 3/1899 | Niemann |
| 796,910 A | 8/1905 | Heman |
| 1,950,378 A | 3/1934 | Andrews |
| 2,163,324 A | 6/1939 | Reinhold |
| 4,046,150 A | 9/1977 | Schwartz et al. |
| 4,299,225 A | 11/1981 | Glassman |
| 4,347,846 A | 9/1982 | Dormia |
| 4,425,908 A | 1/1984 | Simon |
| 4,619,246 A | 10/1986 | Molgaard-Nielsen et al. |
| 4,727,873 A | 3/1988 | Mobin Uddin |
| 4,909,789 A | 3/1990 | Taguchi et al. |
| 4,990,156 A | 2/1991 | Lefebvre |
| 5,098,440 A | 3/1992 | Hillstead |

(Continued)

FOREIGN PATENT DOCUMENTS

| CN | 2635045 Y | 8/2004 |
|---|---|---|
| GB | 1588072 | 4/1981 |

(Continued)

OTHER PUBLICATIONS

Johnson et al.; U.S. Appl. No. 13/791,464 entitled "Coated endoluminal filters," filed Mar. 8, 2013.

(Continued)

*Primary Examiner* — Julian W Woo

(57) ABSTRACT

Embodiments of the invention relate generally to devices and methods for providing filtration of debris within a body lumen. More particularly, embodiments of the invention related to devices and methods for providing distal protection to a medical procedure by filtration of debris generated by the medical procedure using filters having a frame with a slidable crossover point.

38 Claims, 28 Drawing Sheets

(56) References Cited

U.S. PATENT DOCUMENTS

| | | | |
|---|---|---|---|
| 5,192,286 A | 3/1993 | Phan et al. | |
| 5,234,458 A | 8/1993 | Metais | |
| 5,342,371 A | 8/1994 | Welter et al. | |
| 5,370,657 A | 12/1994 | Irie | |
| 5,375,612 A | 12/1994 | Cottenceau et al. | |
| 5,601,595 A | 2/1997 | Smith | |
| 5,626,605 A | 5/1997 | Irie et al. | |
| 5,683,411 A | 11/1997 | Kavteladze et al. | |
| 5,725,552 A | 3/1998 | Kotula et al. | |
| 5,733,294 A | 3/1998 | Forber et al. | |
| 5,797,953 A | 8/1998 | Tekulve | |
| 5,814,064 A | 9/1998 | Daniel et al. | |
| RE36,057 E | 1/1999 | Martin | |
| 5,925,060 A | 7/1999 | Forber | |
| 5,944,738 A | 8/1999 | Amplatz et al. | |
| 6,053,925 A | 4/2000 | Barnhart | |
| 6,059,825 A | 5/2000 | Hobbs et al. | |
| 6,066,149 A * | 5/2000 | Samson | A61B 17/221 606/127 |
| 6,080,182 A | 6/2000 | Shaw et al. | |
| 6,099,534 A | 8/2000 | Bates et al. | |
| 6,106,476 A | 8/2000 | Coral et al. | |
| 6,146,404 A | 11/2000 | Kim et al. | |
| 6,171,327 B1 | 1/2001 | Daniel et al. | |
| 6,231,581 B1 | 5/2001 | Shank et al. | |
| 6,346,116 B1 | 2/2002 | Brooks et al. | |
| 6,361,545 B1 | 3/2002 | Macoviak et al. | |
| 6,368,338 B1 | 4/2002 | Konya et al. | |
| 6,375,670 B1 | 4/2002 | Greenhalgh | |
| 6,443,972 B1 | 9/2002 | Bosma et al. | |
| 6,454,775 B1 | 9/2002 | Demarais et al. | |
| 6,458,145 B1 | 10/2002 | Ravenscroft et al. | |
| 6,468,301 B1 | 10/2002 | Amplatz et al. | |
| 6,485,502 B2 | 11/2002 | Don Michael et al. | |
| 6,530,939 B1 | 3/2003 | Hopkins et al. | |
| 6,537,297 B2 | 3/2003 | Tsugita et al. | |
| 6,544,279 B1 | 4/2003 | Hopkins et al. | |
| 6,554,849 B1 | 4/2003 | Jones et al. | |
| 6,610,077 B1 | 8/2003 | Hancock et al. | |
| 6,613,074 B1 | 9/2003 | Mitelberg et al. | |
| 6,626,915 B2 | 9/2003 | Leveillee | |
| 6,638,294 B1 | 10/2003 | Palmer | |
| 6,645,152 B1 | 11/2003 | Jung et al. | |
| 6,652,556 B1 | 11/2003 | VanTassel et al. | |
| 6,740,061 B1 * | 5/2004 | Oslund | A61F 2/013 604/104 |
| 6,776,770 B1 | 8/2004 | Trerotola | |
| 6,783,538 B2 | 8/2004 | McGuckin, Jr. et al. | |
| 6,824,545 B2 | 11/2004 | Sepetka et al. | |
| 6,939,362 B2 | 9/2005 | Boyle et al. | |
| 6,958,074 B2 | 10/2005 | Russell | |
| 7,282,055 B2 | 10/2007 | Tsuruta | |
| 7,306,619 B1 * | 12/2007 | Palmer | A61F 2/013 606/200 |
| 7,582,100 B2 | 9/2009 | Johnson et al. | |
| 7,645,292 B2 | 1/2010 | Porter | |
| 7,655,013 B2 | 2/2010 | Bieneman | |
| 7,695,484 B2 | 4/2010 | Wallace et al. | |
| 7,713,275 B2 | 5/2010 | Greenberg et al. | |
| 7,753,918 B2 | 7/2010 | Hartley et al. | |
| 7,776,052 B2 | 8/2010 | Greenberg et al. | |
| 7,785,343 B2 | 8/2010 | Johnson et al. | |
| 7,789,892 B2 | 9/2010 | Johnson et al. | |
| 7,806,906 B2 | 10/2010 | Don Michael | |
| 7,854,747 B2 | 12/2010 | Johnson et al. | |
| 7,875,038 B2 | 1/2011 | Que et al. | |
| 8,057,506 B2 | 11/2011 | Gilson et al. | |
| 8,162,974 B2 | 4/2012 | Eskuri et al. | |
| 8,226,679 B2 | 7/2012 | Johnson et al. | |
| 9,017,364 B2 * | 4/2015 | Fifer | A61F 2/013 606/200 |
| 9,827,084 B2 * | 11/2017 | Bonnette | A61B 17/221 |
| 2001/0003801 A1 | 6/2001 | Strecker | |
| 2001/0039432 A1 | 11/2001 | Whitcher et al. | |
| 2001/0039450 A1 | 11/2001 | Pavcnik et al. | |
| 2002/0004667 A1 | 1/2002 | Adams et al. | |
| 2002/0022832 A1 | 2/2002 | Mikus et al. | |
| 2002/0022858 A1 | 2/2002 | Demond et al. | |
| 2002/0045916 A1 | 4/2002 | Gray et al. | |
| 2002/0072730 A1 | 6/2002 | McGill et al. | |
| 2002/0091408 A1 | 7/2002 | Sutton et al. | |
| 2002/0099437 A1 | 7/2002 | Anson et al. | |
| 2002/0107541 A1 | 8/2002 | Vale et al. | |
| 2002/0120287 A1 | 8/2002 | Huter | |
| 2002/0161393 A1 * | 10/2002 | Demond | A61F 2/01 606/200 |
| 2002/0183783 A1 | 12/2002 | Shadduck | |
| 2002/0193826 A1 | 12/2002 | McGuckin et al. | |
| 2003/0040772 A1 | 2/2003 | Hyodoh et al. | |
| 2003/0069596 A1 | 4/2003 | Eskuri | |
| 2003/0083735 A1 | 5/2003 | Denardo et al. | |
| 2003/0097094 A1 | 5/2003 | Ouriel et al. | |
| 2003/0097114 A1 | 5/2003 | Ouriel et al. | |
| 2003/0130681 A1 | 7/2003 | Ungs | |
| 2003/0130684 A1 | 7/2003 | Brady et al. | |
| 2003/0171774 A1 | 9/2003 | Freudenthal et al. | |
| 2003/0171803 A1 | 9/2003 | Shimon | |
| 2003/0187495 A1 | 10/2003 | Cully et al. | |
| 2003/0208224 A1 | 11/2003 | Broome | |
| 2003/0212429 A1 | 11/2003 | Keegan et al. | |
| 2004/0093017 A1 | 5/2004 | Chanduszko | |
| 2004/0122466 A1 | 6/2004 | Bales | |
| 2004/0153118 A1 | 8/2004 | Clubb et al. | |
| 2004/0199201 A1 | 10/2004 | Kellett et al. | |
| 2004/0220608 A1 | 11/2004 | D'Aquanni et al. | |
| 2004/0236368 A1 | 11/2004 | McGuckin et al. | |
| 2004/0254601 A1 | 12/2004 | Eskuri | |
| 2005/0080481 A1 | 4/2005 | Madda et al. | |
| 2005/0107822 A1 | 5/2005 | WasDyke | |
| 2005/0154416 A1 | 7/2005 | Herweck et al. | |
| 2006/0020285 A1 | 1/2006 | Niermann | |
| 2006/0020286 A1 | 1/2006 | Niermann | |
| 2006/0069405 A1 | 3/2006 | Schaeffer et al. | |
| 2006/0100658 A1 | 5/2006 | Obana et al. | |
| 2006/0111770 A1 | 5/2006 | Pavcnik et al. | |
| 2006/0149312 A1 | 7/2006 | Arguello et al. | |
| 2006/0149313 A1 | 7/2006 | Arguello et al. | |
| 2006/0195137 A1 | 8/2006 | Sepetka et al. | |
| 2006/0229638 A1 | 10/2006 | Abrams et al. | |
| 2006/0241676 A1 | 10/2006 | Johnson | |
| 2006/0241677 A1 | 10/2006 | Johnson et al. | |
| 2006/0241678 A1 | 10/2006 | Johnson et al. | |
| 2006/0241679 A1 | 10/2006 | Johnson et al. | |
| 2006/0253148 A1 | 11/2006 | Leone et al. | |
| 2007/0112371 A1 | 5/2007 | Cangialosi et al. | |
| 2007/0123932 A1 | 5/2007 | Gray et al. | |
| 2008/0004687 A1 | 1/2008 | Barbut et al. | |
| 2008/0021497 A1 | 1/2008 | Johnson et al. | |
| 2008/0033482 A1 | 2/2008 | Kusleika | |
| 2008/0086149 A1 | 4/2008 | Diamant et al. | |
| 2008/0147111 A1 | 6/2008 | Johnson et al. | |
| 2009/0306704 A1 | 12/2009 | Johnson | |
| 2009/0326575 A1 | 12/2009 | Galdonik et al. | |
| 2010/0185231 A1 | 7/2010 | Lashinski | |
| 2010/0191276 A1 | 7/2010 | Lashinski | |
| 2010/0268265 A1 | 10/2010 | Krolik et al. | |
| 2010/0318115 A1 | 12/2010 | Chanduszko et al. | |
| 2010/0324590 A1 | 12/2010 | Johnson et al. | |
| 2011/0022076 A1 | 1/2011 | Lashinski | |
| 2011/0034718 A1 | 2/2011 | Nakazawa | |
| 2011/0264106 A1 | 10/2011 | Taube et al. | |
| 2011/0282379 A1 | 11/2011 | Lee et al. | |
| 2012/0010650 A1 | 1/2012 | Sos | |
| 2012/0179196 A1 | 7/2012 | Johnson et al. | |
| 2012/0289996 A1 * | 11/2012 | Lee | A61F 2/013 606/200 |
| 2013/0035715 A1 | 2/2013 | Johnson et al. | |
| 2013/0184744 A1 | 7/2013 | Johnson et al. | |
| 2013/0190804 A1 | 7/2013 | Johnson et al. | |

FOREIGN PATENT DOCUMENTS

| | | |
|---|---|---|
| JP | 10-509623 | 9/1998 |
| WO | WO 01/49185 A1 | 7/2001 |

(56) References Cited

FOREIGN PATENT DOCUMENTS

| WO | WO 02/02162 A2 | 1/2002 |
|---|---|---|
| WO | WO 2005/102211 A1 | 11/2005 |
| WO | WO 2006/034233 A1 | 3/2006 |
| WO | WO 2009/086482 A1 | 7/2009 |
| WO | 2011034718 A2 | 3/2011 |
| WO | WO 2012/003369 A2 | 1/2012 |
| WO | WO 2012/031149 A1 | 3/2012 |
| WO | WO 2012092377 A1 | 7/2012 |
| WO | WO 2012/118696 A1 | 9/2012 |

OTHER PUBLICATIONS

Johnson et al.; U.S. Appl. No. 13/802,657 entitled "Distal protection device," filed Mar. 13, 2013.

Johnson et al.; U.S. Appl. No. 13/919,630 entitled "Methods for Maintaining a Filtering Device Within a Lumen," filed Jun. 17, 2013.

Johnson et al.; U.S. Appl. No. 13/919,658 entitled "Biodegradable Implant Device," filed Jun. 17, 2013.

Johnson et al.; U.S. Appl. No. 13/919,680 entitled "Endoluminal Filter," filed Jun. 17, 2013.

Johnson et al.; U.S. Appl. No. 13/919,718 entitled "Endoluminal Filter," filed Jun. 17, 2013.

Johnson et al.; U.S. Appl. No. 13/931,462 entitled "Retrievable Endoluminal Filter" filed Jun. 28, 2013.

Johnson et al.; U.S. Appl. No. 13/931,408 entitled "Endoluminal Filter," filed Jun. 28, 2013.

Johnson et al.; U.S. Appl. No. 13/931,334 entitled "Filter Delivery Methods," filed Jun. 28, 2013.

Johnson et al.; U.S. Appl. No. 13/931,256 entitled "Methods for Maintaining a Filtering Device Within a Lumen," filed Jun. 28, 2013.

Laroya et al.; U.S. Appl. No. 13/475,819 entitled "Retrieval Snare Device and Method," filed May 18, 2012.

Johnson et al.; U.S. Appl. No. 13/553,335 entitled "Endoluminal Filter With Fixation," filed Jul. 19, 2012.

Kahraman et al.; The Diameters of the Aorta and Its Major Branches in Patients with Isolated Coronary Artery Ectasia; Tex Heart Inst J.; vol. 33, No. 4: pp. 463R468; (month unavailable) 2006.

Millward, Steven F.; Temporary and retrievable inferior vena cava filters; JVIR; vol. 9; No. 3; pp. 381-387, May/Jun. 1998.

Siskin, Gary P.; Inferior Vena Cava Filters; eMedicine; Sep. 7, 2004.

Streiff, Michael B.; Vena caval filters; a comprehensive review; Blood; vol. 95; No. 12; pp. 3669-3677; Jun. 15, 2000.

Laroya et al.; U.S. Appl. No. 14/458,168 entitled "Retrieval Snare Device and Method," filed Aug. 12, 2014.

Johnson et al.; U.S. Appl. No. 14/372,180 entitled "Endoluminal Filter With Fixation," filed Jul. 14, 2014.

Johnson et al.; U.S. Appl. No. 14/574,203 entitled "Filter support members," filed Dec. 17, 2014.

Johnson et al.; U.S. Appl. No. 14/575,935 entitled "Extended anchor endoluminal filter," filed Dec. 18, 2014.

Johnson et al.; U.S. Appl. No. 14/578,087 entitled "Devices and methods for controlled endoluminal filter deployment," filed Dec. 19, 2015.

Johnson et al.; U.S. Appl. No. 14/581,638 entitled "Treatment structure and methods of use," filed Dec. 23, 2014.

Laroya et al.; U.S. Appl. No. 13/739,828 entitled "Retrieval Snare Device and Method," filed Jan. 11, 2013.

\* cited by examiner

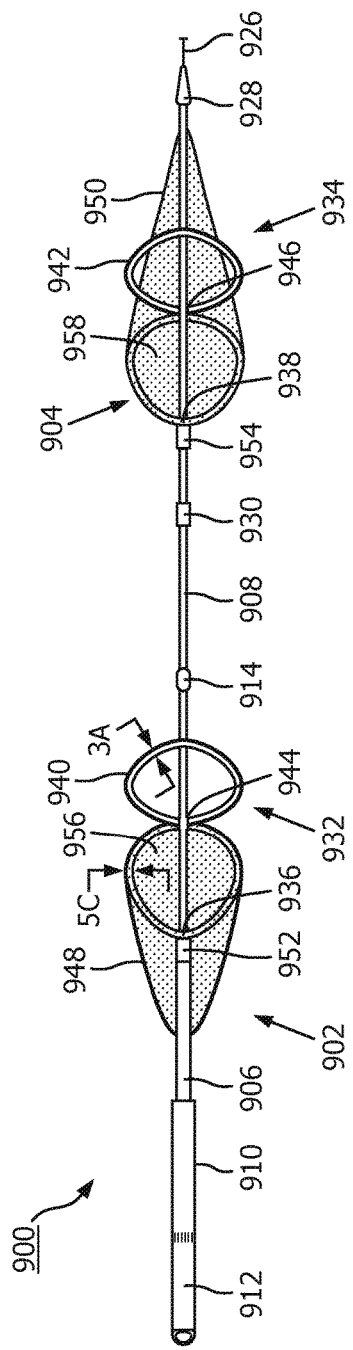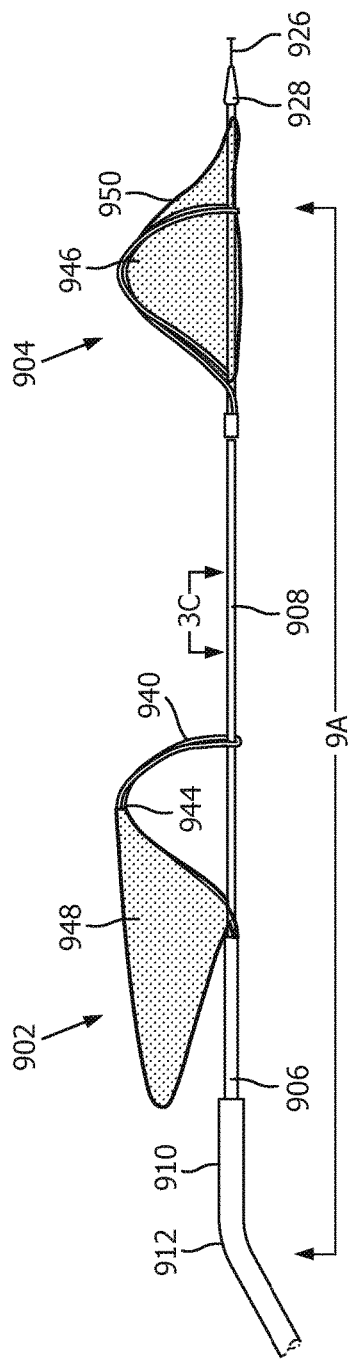
FIG. 9A
FIG. 9B

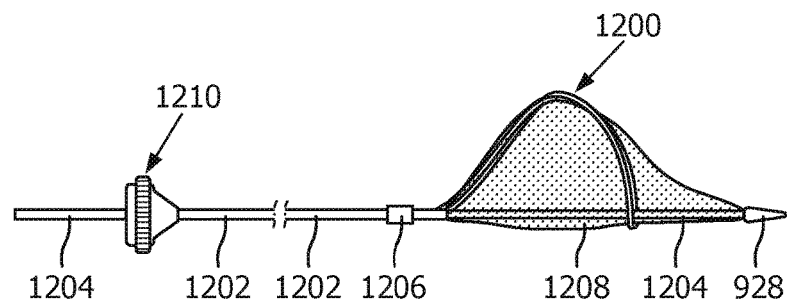
FIG. 12A
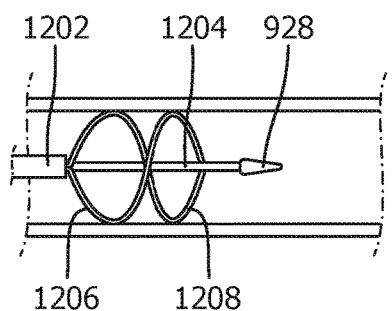     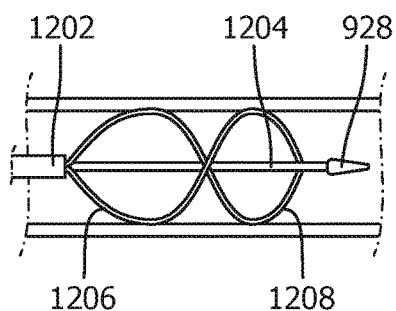
FIG. 12B          FIG. 12C
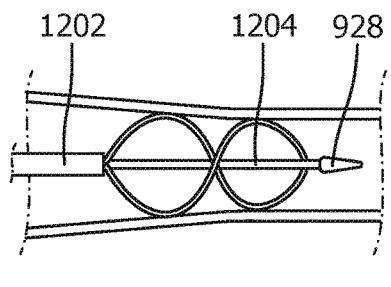     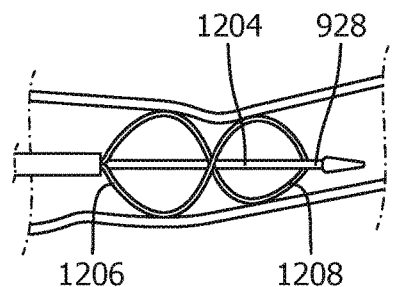
FIG. 12D          FIG. 12E

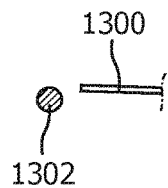 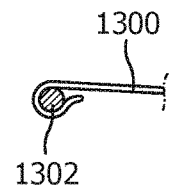 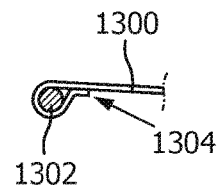
FIG. 13A  FIG. 13B  FIG. 13C
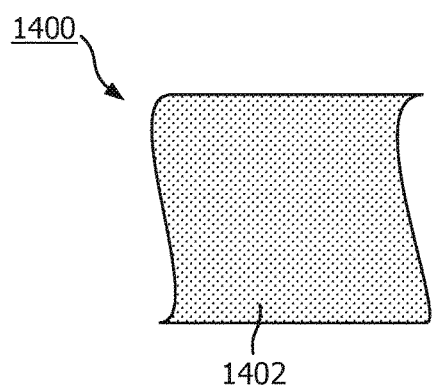
FIG. 14A
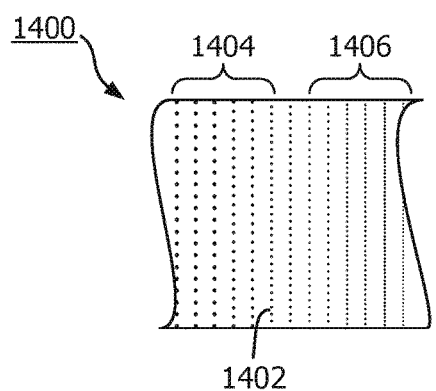
FIG. 14B

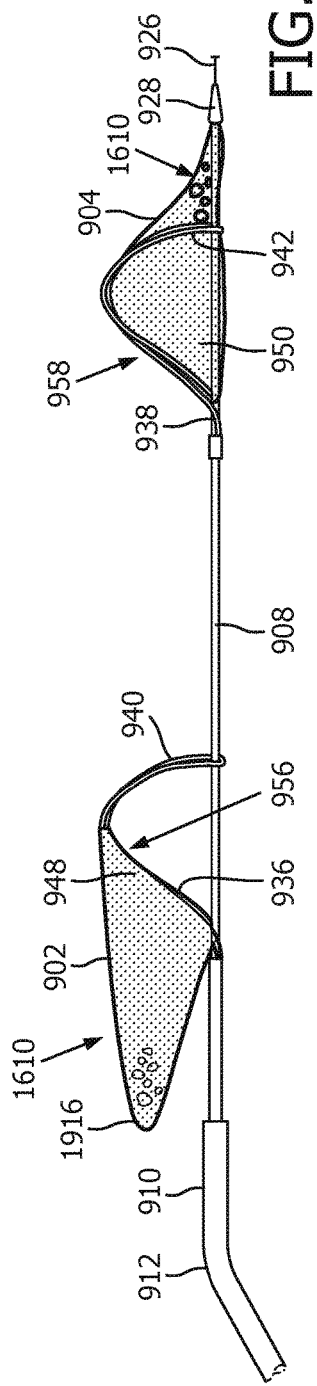
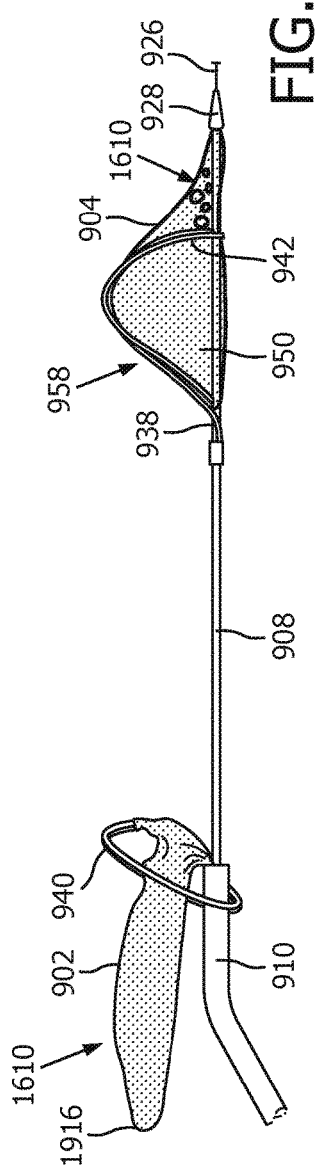
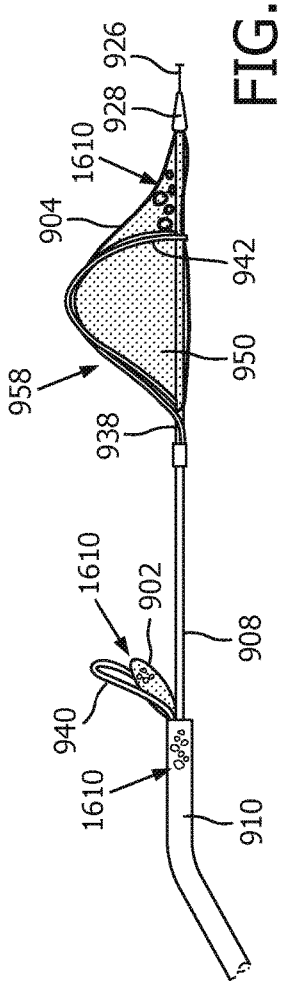

DISTAL PROTECTION FILTER

CROSS REFERENCE TO RELATED APPLICATIONS

This application claims the benefit of U.S. Provisional Application No. 61/607,191, filed Mar. 6, 2012, which is hereby incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference. This application is related to U.S. application Ser. No. 11/325,247, now issued as U.S. Pat. No. 7,789,892, which is hereby incorporated by reference in its entirety.

FIELD

Embodiments of the invention relate generally to devices and methods for providing filtration of debris within a body lumen. More particularly, embodiments of the invention related to devices and methods for providing distal protection to a medical procedure by filtration of debris generated by the medical procedure.

BACKGROUND

Embolic protection is utilized throughout the vasculature to prevent the potentially fatal passage of embolic material, calcium deposits, and other debris in the bloodstream to smaller vessels where it can obstruct blood flow. The dislodgement of embolic material, calcium deposits, and other debris is often associated with procedures which open blood vessels to restore natural blood flow such as stenting, angioplasty, arthrectomy, valve replacement or repair, endarterectomy or thrombectomy. Used as an adjunct to these procedures, embolic protection devices trap debris and provide a means for removal from the body.

For example, in a percutaneous aortic valve replacement procedure as shown in FIGS. 1A and 1B, a valve delivery catheter 10 can be inserted through the lumen 13 of the aorta 12, via the descending aorta 14, the aortic arch 16, the ascending aorta 18, and to the native aortic valve 20 of the heart. During insertion through the aortic arch 16, the valve delivery catheter 10 has a tendency to make contact with the upper portion 32 of the aortic arch 16 as it traverses the bend between the descending aorta 14 and ascending aorta 18. During the aortic valve replacement procedure, embolic debris, calcium deposits and other debris can be generated and/or loosened from the native valve leaflets. This debris can travel through arteries branching off the aorta 12, such as the brachiocephalic trunk 22, which splits into the right subclavian artery 24 and the right common carotid artery 26, the left common carotid artery 28, and the left subclavian artery 30. Debris that passes into the right common carotid 26 and left common carotid artery 28 can travel to and get lodged within vessels supplying blood to the brain, potentially causing a stroke.

Accordingly, it would be desirable to provide a system and method for providing embolic protection to the right common carotid artery and the left common carotid artery in order to reduce complications, such as stroke, that may occur during a variety of medical procedures as described herein.

SUMMARY OF THE DISCLOSURE

The present invention relates generally to devices and methods for providing filtration of debris within a body lumen. More particularly, embodiments of the invention related to devices and methods for providing distal protection to a medical procedure by filtration of debris generated by the medical procedure.

Variations and modifications of the devices and methods disclosed herein will be readily apparent to persons skilled in the art. As such, it should be understood that the foregoing summary, detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

In some embodiments, a system for providing embolic protection is provided. The system includes a first sheath having a proximal end, a distal end and a lumen, the lumen configured to receive a guidewire; a first distal protection filter attached to a distal portion of the first sheath, the first distal protection filter comprising a self-expanding frame with a slidable crossover point that defines a proximal loop and a distal loop, and a filter element attached to one of the proximal loop or distal loop of the self-expanding frame of the first distal protection filter, wherein the crossover point is proximate to the filter element; a second sheath having a proximal end, a distal end and a lumen, the second sheath disposed over the first sheath, wherein the distal end of the second sheath is located proximally the first distal protection filter; a second distal protection filter attached to a distal portion of the second sheath, the second distal protection filter comprising a self-expanding frame with a slidable crossover point that defines a proximal loop and a distal loop, and a filter element attached to the proximal loop of the self-expanding frame of the second distal protection filter, wherein the crossover point is proximal to the filter element; and an outer sheath disposed over both the first sheath and the second sheath.

In some embodiments, the filter element of the second distal protection filter has a mouth and an apex, wherein the mouth of the filter element is attached to the proximal loop and the apex is unattached to the sheath.

In some embodiments, the first sheath includes a stop portion proximal the first distal protection filter, wherein the stop portion is configured to stop advancement of the second sheath proximal to the stop portion.

In some embodiments, in a stowed configuration within the outer sheath, the filter element of the first distal protection filter has a mouth facing the second distal protection filter and the filter element of the second distal protection filter has a mouth facing the first distal protection filter.

In some embodiments, the distance between the first distal protection filter and the second distal protection filter is adjustable. In some embodiments, the position of the first sheath and the position of the second sheath are independently lockable, allowing one of the first sheath and the second sheath to be locked in position while the position of the other sheath adjusted.

In some embodiments, the self-expanding frame of the first distal protection filter includes at least one anchor element. In some embodiments, the self-expanding frame of the second distal protection filter includes at least one anchor element. In some embodiments, the at least one anchor element of the first distal protection filter is configured to partially penetrate through the vessel wall. In some embodiments, the first sheath includes at least one anchor proximal the first distal protection filter. In some embodiments, the at least one anchor is located on a side of the first sheath opposite the crossover point of the first distal protection filter. In some embodiments, the at least one anchor is configured to be located within the aortic arch of a patient when the first distal protection filter is deployed from the outer sheath. In some embodiments, the at least one anchor of the first sheath is configured to partially penetrate through the vessel wall.

In some embodiments, the filter elements of both the first distal protection filter and the second distal protection filter include a plurality of pores with a diameter of less than about 200 microns. In some embodiments, the pores of the filter elements of both the first distal protection filter and the second distal protection filter are distributed more densely in the peripheral portion of the filter elements. In some embodiments, the pores of the filter elements of both the first distal protection filter and the second distal protection filter are larger in the peripheral portion of the filter elements than in the central portion of the filter elements. In some embodiments, the pores of the filter elements are oblong shaped. In some embodiments, the filter elements comprise filter membranes with laser drilled holes.

In some embodiments, the filter elements comprise polymer fibers that are selected from the group consisting of electrospun fibers, knitted fibers, braided fibers, and woven fibers. In some embodiments, the filter elements are made from a polymer selected from the group consisting of polyurethane, polyethylene, and nylon.

In some embodiments, the filter elements of both the first distal protection filter and the second distal protection filter have an open area between about 25 to 75 percent.

In some embodiments, the outer sheath is 9 Fr or less.

In some embodiments, the self-expanding frames of both the first distal protection filter and the second distal protection filter include a radiopaque marker. In some embodiments, the radiopaque marker is a radiopaque coil of wire wrapped around a superelastic core.

In some embodiments, the distal loops of both the first distal protection filter and the second distal protection filter are unattached to either the first sheath or second sheath.

In some embodiments, the outer sheath includes a curved distal portion with a curvature between about 15 to 45 degrees.

In some embodiments, the first distal protection filter and second distal protection filter are coated with a drug. In some embodiments, the drug is heparin.

In some embodiments, the proximal loop of the first distal protection filter is attached to first sheath, and the proximal loop of the second distal protection filter is attached to the second sheath. In some embodiments, the distal loop of the first distal protection filter is attached to first sheath, and the proximal loop of the second distal protection filter is attached to the second sheath.

In some embodiments, the self-expanding frame comprises a single wire element shaped in a figure eight configuration.

In some embodiments, the system further includes a hub, the hub having a first hub portion that is engaged with the proximal portion of the first sheath, a second hub portion that is engaged with the proximal portion of the second sheath, and a third hub portion that is engaged with the proximal portion of the outer sheath, wherein the hub allows the first sheath, the second sheath, and the outer sheath to be independently manipulated. In some embodiments, the third hub portion is removable and configured to allow the outer sheath to be swapped for another sheath. In some embodiments, each of the first hub portion, the second hub portion and the third hub portion are configured to receive the guidewire.

In some embodiments, the system further includes a deflection mechanism attached to the first sheath at a location between the first distal protection filter and the second distal protection filter after deployment of both distal protection filters. In some embodiments, the deflection mechanism is an inflatable balloon. In some embodiments, the deflection mechanism is a flat shield.

In some embodiments, a method of providing embolic protection to at least two blood vessels is provided. The method includes advancing a first distal protection filter to a first location in a first blood vessel, wherein the first distal protection filter includes a first self-expanding frame, and a first filter element having a mouth and an apex with the mouth attached to the first self-expanding frame; deploying the first distal protection filter at the first location; manipulating a second distal protection filter to a second location in a second blood vessel, wherein the second distal protection filter includes a second self-expanding frame and a second filter element having a mouth and an apex with the mouth attached to the second self-expanding frame; deploying the second distal protection filter at the second location; performing a procedure in a portion of the vasculature that releases or generates particulate debris; and capturing the particulate debris with one or more of the first distal protection filter and the second distal protection filter.

In some embodiments, the method further includes advancing an outer sheath over the mouth of the second filter element to close the mouth of the second filter element before advancing the outer sheath over the apex of the second filter element; and advancing the outer sheath over the mouth of the first filter element to close the mouth of the first filter element before advancing the outer sheath over the apex of the first filter element.

In some embodiments, the first distal protection filter is deployed in the left common carotid artery and the second distal protection filter is deployed in the brachiocephalic trunk.

In some embodiments, the method further includes adjusting the length between the first distal protection filter and the second distal protection filter. In some embodiments, the length is adjusted by fixing the location of the first distal protection filter, and then manipulating the position of the second distal protection filter.

In some embodiments, the method further includes conforming a sheath attached to the first distal protection filter to the upper surface of the aortic arch between the left common carotid artery and the brachiocephalic trunk. In some embodiments, the method further includes conforming a sheath attached to the first distal protection filter along the inner wall of the aortic arch from the outer radius of the aortic arch proximate the left common carotid artery to the inner radius of the aortic arch and to the outer radius of the aortic arch proximate the brachiocephalic trunk.

In some embodiments, the first self-expanding frame includes a slidable crossover point that defines a proximal loop and a distal loop, and wherein the second self-expanding frame includes a slidable crossover point that defines a proximal loop and a distal loop with the mouth of the second filter element attached to the proximal loop of the second self-expanding frame.

In some embodiments, the apex of the second filter element is unattached to the second self-expanding frame.

In some embodiments, the distal loop of first self-expanding frame moves proximally as the mouth of the first filter element is closed such that the distal loop of the first self-expanding frame is proximal the crossover point of the first self-expanding frame during a part of the mouth closure process. In some embodiments, the distal loop of second self-expanding frame moves proximally as the mouth of the second filter element is closed such that the distal loop of the second self-expanding frame is proximal the crossover point of the second self-expanding frame during a part of the mouth closure process.

In some embodiments, the apex of the second filter is unattached to a structure on which the second distal protection filter is attached.

In some embodiments, the method further includes aspirating the debris trapped in either the first distal protection filter or the second distal protection filter.

In some embodiments, the method further includes deploying a deflection mechanism between the first distal protection filter and the second distal protection filter.

In some embodiments, manipulating a second distal protection filter to a second location includes withdrawing the second distal protection filter to the second location. In some embodiments, manipulating a second distal protection filter to a second location includes advancing the second distal protection filter to the second location.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A and 9B illustrate an embodiment of a filtering device with two distal protection filters;

FIGS. 12A-12E illustrate an embodiment of a telescoping distal protection filter that allows control of the length of the filter;

FIGS. 13A-13C illustrate an embodiment of the attachment of a filter material to the frame of the filter;

FIGS. 14A and 14B illustrate embodiments of a filter membrane with various pore distributions;

FIGS. 19A-19F illustrate an embodiment of a method of capturing the distal protection filters using an outer sheath.

DETAILED DESCRIPTION

Figure 1A:
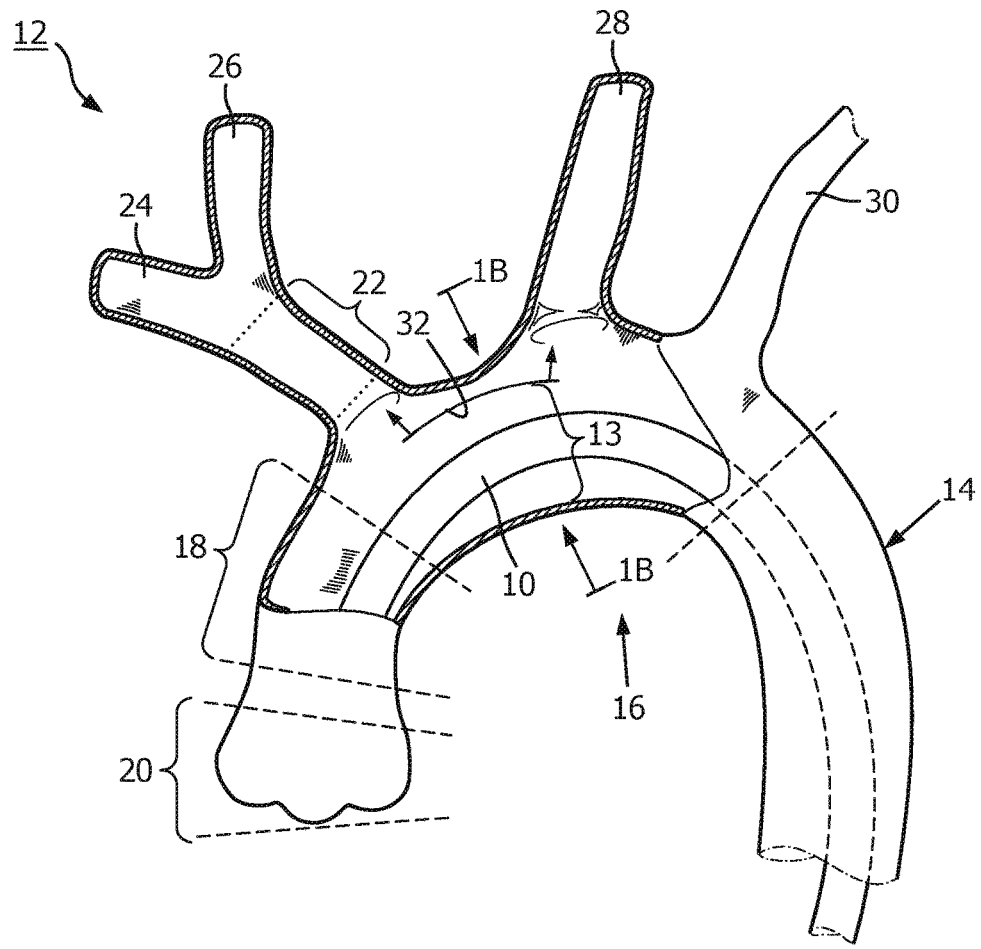
FIG. 1A is a side view of the aorta and its branch arteries with a catheter inserted within the aortic lumen.
Figure 1B:
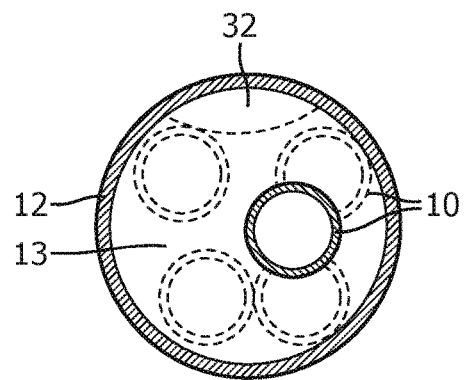
FIG. 1B is a cross-section view of the aorta with a catheter within the aortic lumen.
Figure 2A:
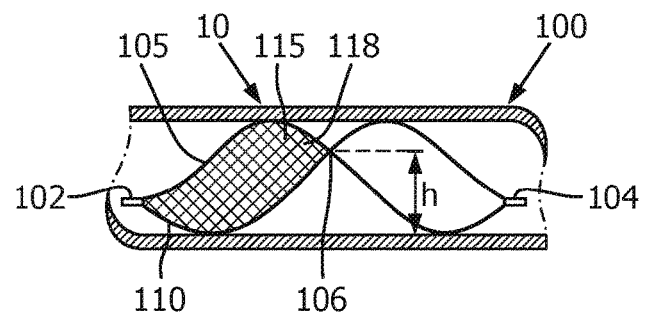
FIGS. 2A-2C illustrate the response of an embodiment of a filtering device to changes in lumen size.

FIG. 2A illustrates an embodiment of a filtering device 100 of the present invention positioned within a lumen 10. The lumen 10 is cut away to show the position of filter 100 deployed into within a lumen and in contact with the lumen wall. The filter 100 includes a first elongate member 105 and a second elongate member 110. In some embodiments, the two elongate members can be opposing helical spirals. The elongate members are joined to form ends 102, 104. The elongate members cross but are not joined to one another at crossover 106, which can be slidable. In one embodiment, the elongate members have first and second sections. First sections extend between the end 102 and the crossover 106 and the second sections extend from the crossover 106 to the second end 104. While some embodiments contact the lumen in different ways, the illustrated embodiment has the ends 102, 104 against one side of the lumen interior wall while the crossover 106 contacts the other side of the lumen interior wall with the elongate bodies in constant or nearly constant apposition along the lumen interior wall between the ends 102, 104. In some embodiments, the diameter of the elongate members can be about 0.003, 0.004, 0.005, 0.006, 0.007, 0.008, 0.009, or 0.010 inches. Using a smaller diameter wire allows the filter to have a lower collapsed profile. In some embodiments, the filters can be collapsed into a 10 Fr, 9 Fr, 8 Fr, 7 Fr, 6 Fr, or 5 Fr or smaller delivery catheter. In some embodiments, the elongate members can be made from a flexible, biocompatible, fatigue-resistant material such as but not limited to nickel-titanium alloys, stainless steel, cobalt chrome, other shape memory alloys, other metal alloys, and various polymers such as PEEK, PTFE, and the like.

Figure 2B:
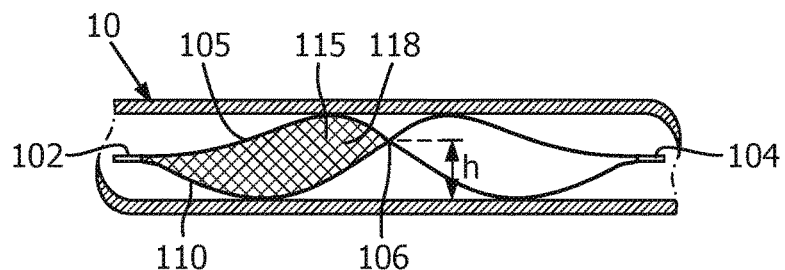
Figure 2C:
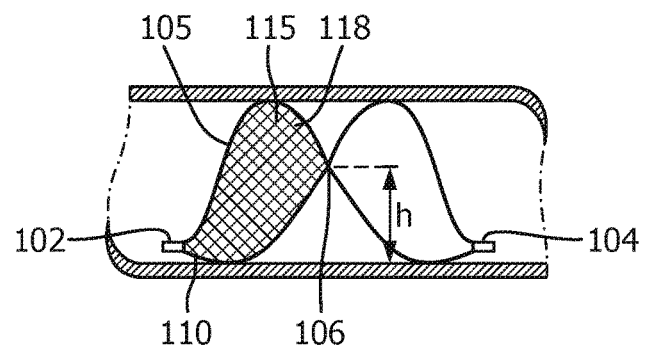

FIGS. 2B and 2C illustrate how the elongate support structure elements of embodiments of the present invention are configured to collapse and expand with natural vessel movements while maintaining constant apposition with the vessel wall. FIGS. 2A, 2B and 2C also illustrate how devices according to embodiments of the present invention are both radially and axially elastic. In response to vessel size changes, ends 102, 104 move out as the vessel size decreases (FIG. 2B) and then move in as the vessel size increases (FIG. 2C). In addition, the device height "h" (measured from the lumen wall in contact with ends 102, 104 to crossover) also changes. Device height "h" changes in direct relation to changes in vessel diameter (i.e., vessel diameter increases will increase device height "h"). As such, device height ("h") in FIG. 2C is greater than device height ("h") in FIG. 2A which is in turn greater than the device height ("h") in FIG. 2B.

FIGS. 2A, 2B and 2C also illustrate how a single sized device can be used to accommodate three different lumen diameters. FIG. 2C illustrates a large lumen, FIG. 2A a medium sized lumen and FIG. 2B a small sized lumen. As these figures make clear, one device can adapt to cover a range of vessel sizes, thereby forming a better seal and providing good wall apposition over a wide range of vessel diameters. Also illustrated is the static or nearly static filter capacity of the material capture structure 115 in some embodiments. In these embodiments, in each different vessel size, the material capture structure 115, the filaments 118 and filter cell 119 maintain the same or nearly the same shape and orientation within the support frame formed by the elongate bodies. These figures also illustrate the dynamic shape changing aspect of the device that may also be used to accommodate and conform to vessel irregularities, tortuosity, flares and tapers and while remaining in apposition to the wall. Because each elongate body may move with a high degree of independence with respect to the other, the loops or support frames formed by the elongate bodies can also independently match the shape/diameter of the lumen section in which it is placed.

For example, a single sized device can be used in a variety of vessels, such as the brachiocephalic trunk and left common carotid artery. The brachiocephalic trunk generally has a diameter between about 6 mm to about 20 mm or larger, and usually between about 8 mm to about 12 mm, or about 8 to 10 mm. The left common carotid artery generally has a diameter between about 5 mm to about 11 mm, and usually between about 6 mm to about 10 mm, or about 7 to 8 mm. Examples of the diameters of the aorta and its major branch arteries are disclosed in Kahraman et al., *The Diameters of the Aorta and Its Major Branches in Patients with Isolated Coronary Artery Ectasia*, Tex Heart Inst J 2006; 33:463-8, which is hereby incorporated by reference in its entirety. In some embodiments, a filter device with a nominal diameter size of about 6 mm, 9 mm, 12 mm, 15 mm, or 18 mm or between about 6 to 18 mm, can be used in the brachiocephalic trunk or left common carotid artery. Because these filter devices cover a dynamic range of sizes, as illustrated in FIGS. 2A-2C, a single filter can used to cover all or a wide range, such as the lower half/upper half or the lower third/middle third/upper third, of typical brachiocephalic trunk and/or left common carotid artery sizes. In some embodiments, the filter devices placed in the brachiocephalic trunk and left common carotid artery can have the same nominal diameter size, while in other embodiments the filter device placed in the left common carotid artery can be smaller than the filter device placed in the brachiocephalic trunk.

Figure 3A:
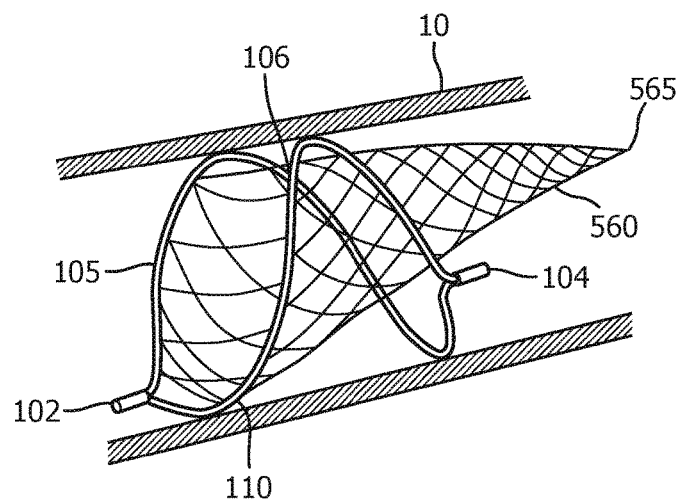
FIGS. 3A and 3B illustrate embodiments of the distal protection filter with a filter element having an attached apex and an unattached apex.
Figure 3B:
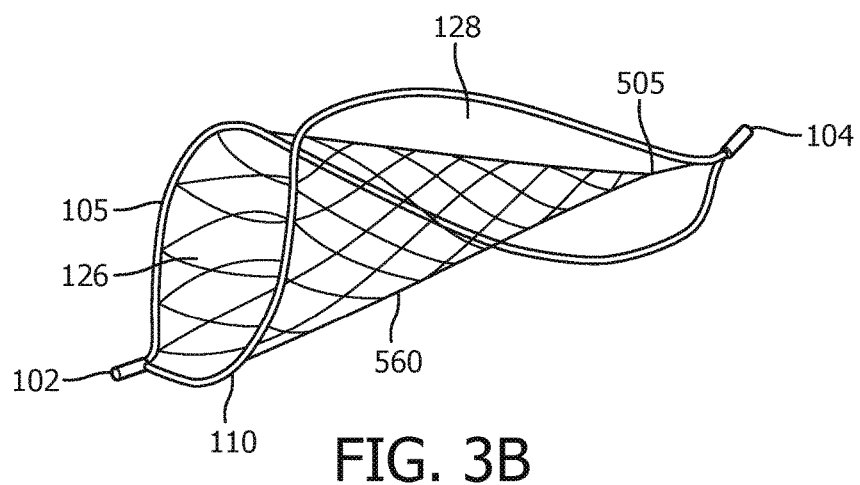

FIGS. 3A-4F illustrate the use of nets or other web structures within the filtering device. The various net structure embodiments described herein are used as material capture structures within filter device embodiments of the present invention. Each of these alternative is illustrated in a support structure similar to that of device 100 in FIG. 2A and elsewhere. When deployed within the lumen 10, the material capture structure 560 has a defined shape such as a cone with a discrete apex 565 (FIG. 3A). In this embodiment, the net structure is long enough to contact the sidewall of the lumen 10 when deployed in the lumen 10. Alternatively, the apex 565 may be attached to the end 104 to keep the net 560 in the lumen flow path and out of contact with the lumen sidewall (FIG. 3B).

Figure 4A:
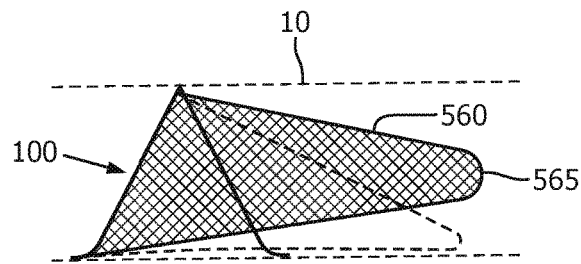
FIGS. 4A-4F illustrate various alternative filtering structures.
Figure 4B:
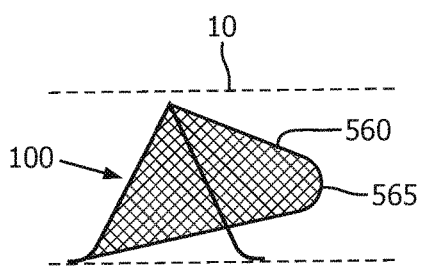
Figure 4C:
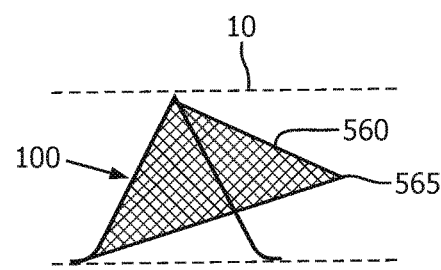
Figure 4D:
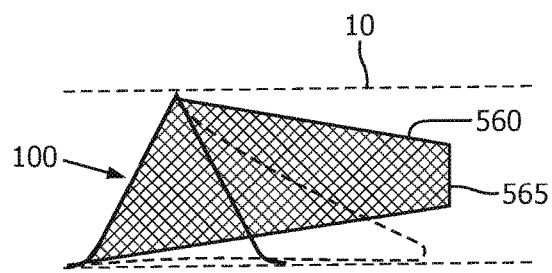
Figure 4E:
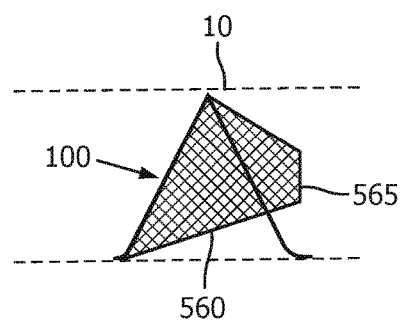
Figure 4F:
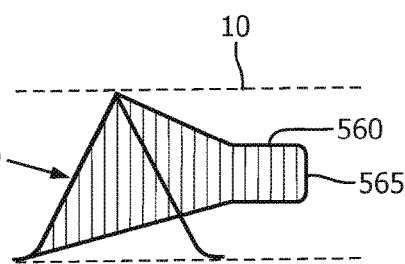

In some embodiments, the apex can be attached to the delivery device, such as the sheath, tube or wire of the delivery device. In other embodiments, the apex can be free, or in other words is unattached to the sheath, tube or wire of the delivery device or the frame of the filter. In some embodiments with a proximal filter and a distal filter, as illustrated in FIG. 9A, the apex of the proximal filter can remain free while the apex of the distal filter can be attached to the delivery device. In some embodiments, the apex of the distal filter can also remain unattached to the sheath. Allowing the apex of the proximal filter to remain free allows a sheath to be advanced first over the mouth of the filter to close the filter before being advanced over the rest of the filter. This prevents or reduces the extrusion of trapped debris within the filter during the recovery of the proximal filter. The net 565 may also have a rounded apex 565 (FIG. 4A) or a truncated cone (flat bottom) (FIG. 4D) or a reservoir apex. Alternatively, the net 560 may a discrete apex 565 so short that it will not contact the lumen sidewall when deployed (FIG. 4B). The short net may also have a rounded apex 565 (FIG. 4B), a flat apex (FIG. 4E) or a sharp apex (FIG. 4C). In addition, the net 560 may have a compound apex 565 (FIG. 4F).

Figure 5A:
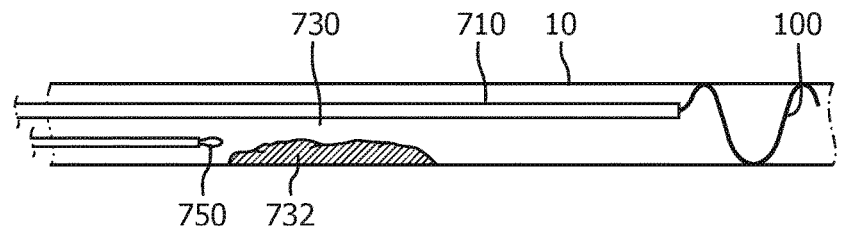
FIGS. 5A-8F illustrate several exemplary methods of using a filtering device.
Figure 5B:
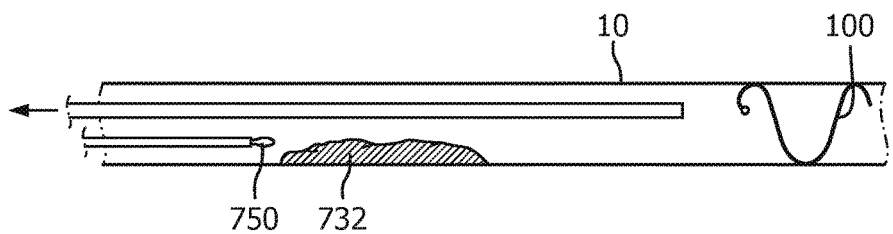
Figure 5C:
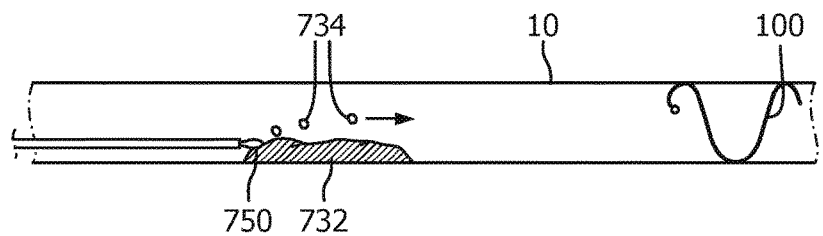
Figure 5D:
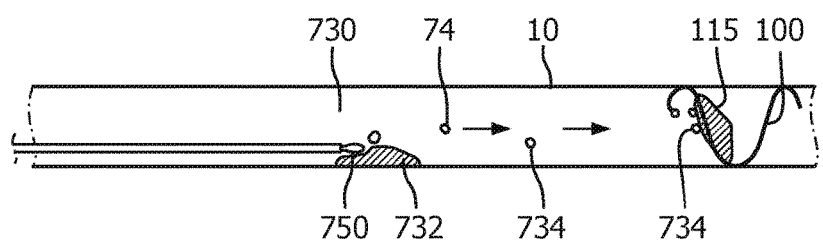
Figure 5E:
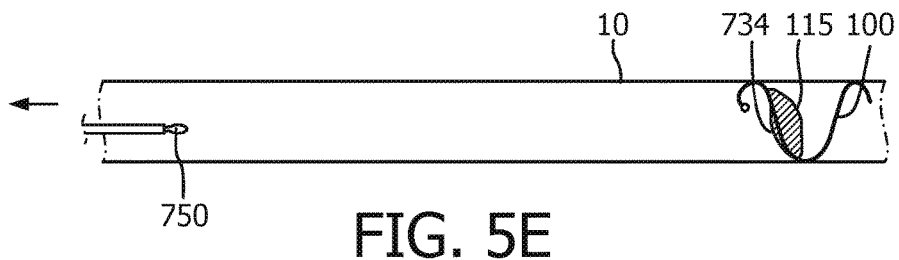
Figure 5F:
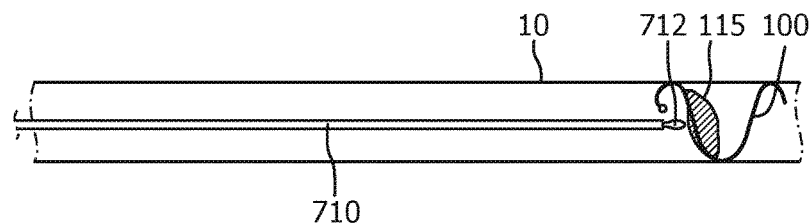

Embodiments of filter devices of the present invention may be used in methods of providing distal protection in procedures such as, for example, thrombectomy, arthrectomy, stenting, angioplasty, valve repair or replacement, stent grafting and other procedures taking place in the heart or circulatory system. It is to be appreciated that embodiments of filter devices of the present invention may be used in veins and arteries. An exemplary procedure is illustrated in FIGS. 5A-I and FIGS. 6A-E. In each procedure, the device 100 is positioned in an un-tethered fashion adjacent to the treatment region 730. The sequence FIGS. 5A-I illustrate the delivery sheath 710 positioning FIG. 5A, complete deployment FIG. 5B into the lumen 10. A conventional treatment device 750 using mechanical, electrical energy or other suitable method is used to clear the undesired material 732 from the lumen wall (FIG. 5C). Some debris 734 removed from the lumen wall through the use of treatment device 750 is subsequently embolized into the blood stream (FIG. 5C) and trapped by the filter 100 (FIG. 5D). The conventional treatment device 750 is removed (FIG. 5E) and thereafter the advancement of recapture sheath 710 is advanced into recovery position (FIG. 5F).

Figure 5G:
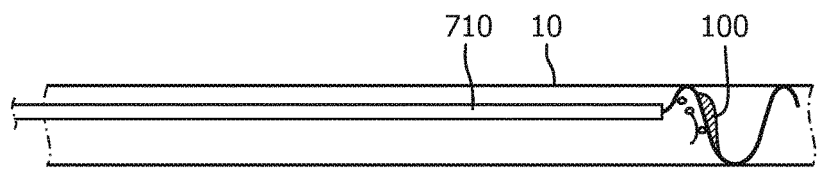
Figure 5H:
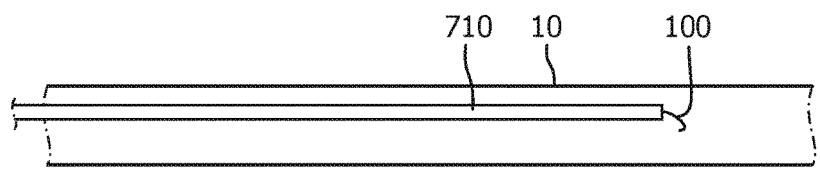
Figure 5I:
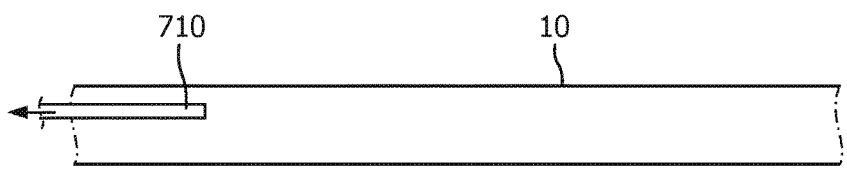

The entrapped debris 734 is then removed prior to recapturing the device with methods such as, for example, aspiration, delivery of therapeutic agents or maceration. Additionally, the device and entrapped debris can be recaptured in whole and removed via the same sheath used to recapture the device as illustrated in FIG. 5G. The device 100 and debris 734 are then withdrawn into the sheath 710 (FIG. 5H), and the sheath withdrawn from the vasculature (FIG. 5I).

Figure 6A:
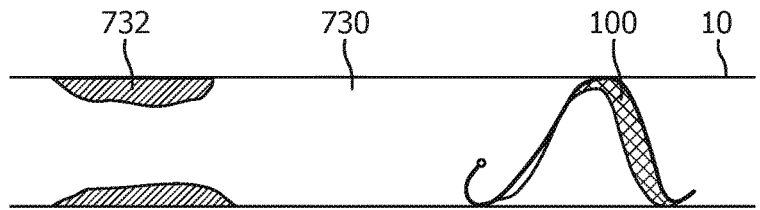
Figure 6B:
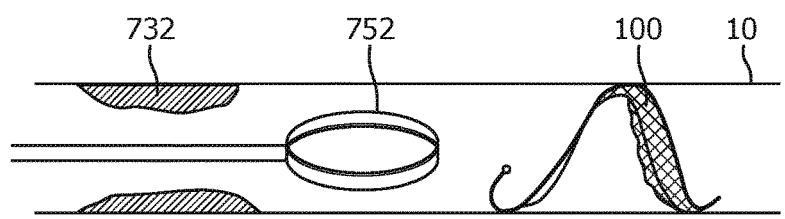
Figure 6C:
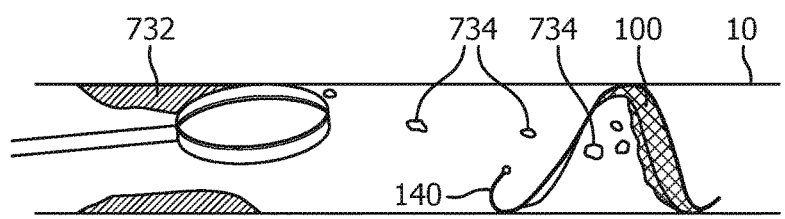
Figure 6D:
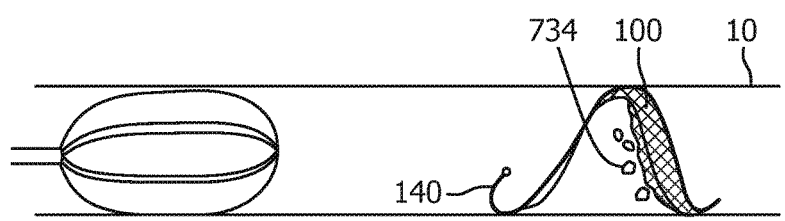
Figure 6E:
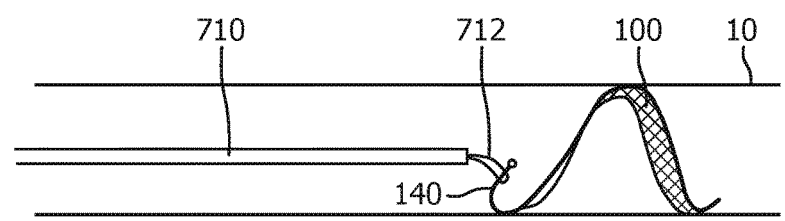

Similarly, an additional use of the invention as un-tethered distal protection is illustrated in FIGS. 6A-E, in which a balloon is used to expand the lesion 732 such as in the case of balloon angioplasty, often performed prior to stenting a vessel to keep it open. For this procedure a balloon catheter is advanced to the lesion site and inflated FIG. 6B, plaque 732 is pushed outward by the balloon (FIG. 6C), thus reestablishing normal blood flow. Any particulate matter 734 embolized by the procedure is trapped by the filter (FIG. 6D). The debris 734 can then be removed prior to filter retrieval as previously described or the device with trapped debris can be removed together.

Untethered filter embodiments can have a retrieval feature 140, such as at the ends of the filter where the elongate members of the frame attach, and anchors, which can be located on the body of the frame to help the filter to maintain its location. In some embodiments, the untethered distal protection filters 100 can be left in the blood vessel to provide protection for up to 12, 24, 48, or 72 hours. In some embodiments, the untethered filters 100 can be left in the blood vessel to provide protection for up to 1 week, 2 weeks, 3 weeks, 4 weeks, 2 months, 3 months, 4 months, 5 months or 6 months. In some embodiments, the untethered filters 100 can be left in the blood vessel perioperatively, i.e. for the duration of the patient's surgical procedure, or sub-chronically, i.e. for a predetermined period of time postoperatively. In some embodiments, periodic aspiration of the debris captured by the filter 100 can be performed to prevent or reduce blockage of the blood flow through the filter 100.

Figure 7A:
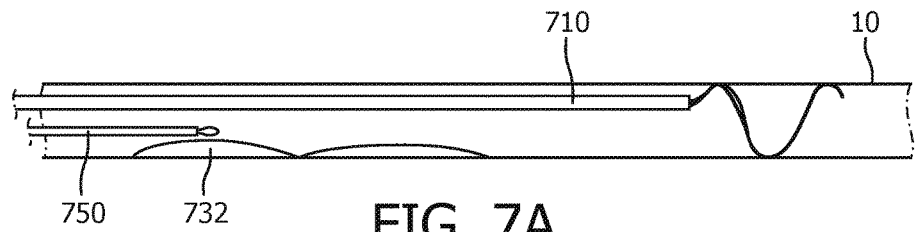
Figure 7B:
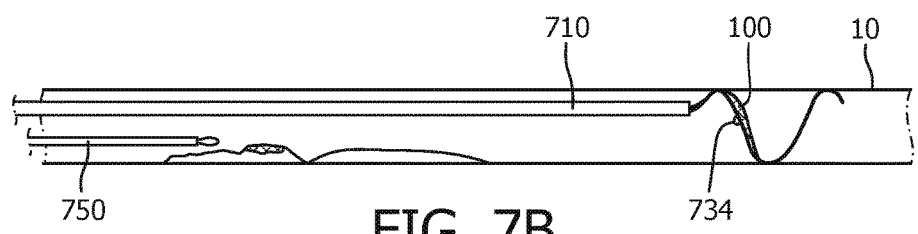

An additional method practiced widely in the art is the use of tethered distal protection adjunctive to the previously described procedures (i.e., the device 100 remains tethered during the procedure). Embodiments of the filtering device of the present invention may also be used for this purpose as illustrated in FIGS. 7A-7E. Positive control of the filter 100 is maintained via an integral wire or snare connected to the device 100. The connection between the integral wire or snare to the device 100 is maintained during the procedure and may be, in some embodiments, used as a guidewire. As illustrated in FIG. 7B, connection to the device 100 is maintained a while performing a procedure to treat the vasculature in proximity to the location (i.e., treat the lesion 732).

Figure 7C:
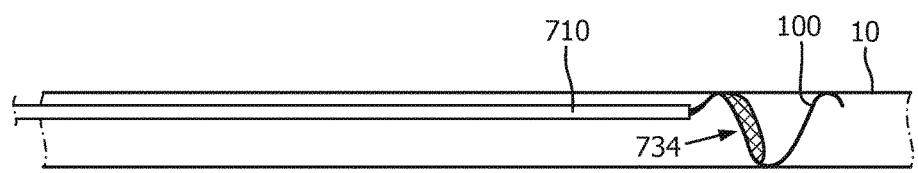
Figure 7D:
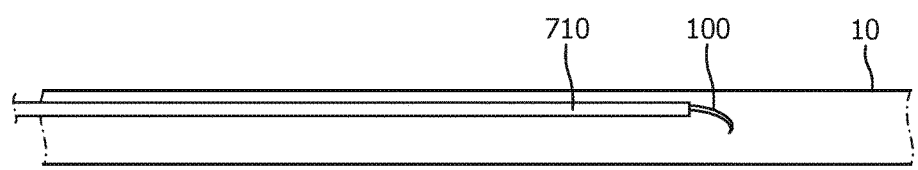
Figure 7E:
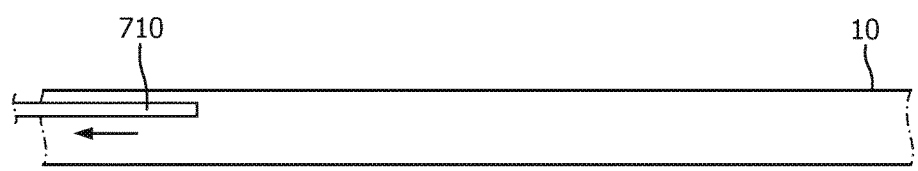

An example of a tethered distal protection method is illustrated in FIGS. 7A-7E. An embodiment of a filter device 100 is deployed distal to the lesion 732 to be treated (FIG. 7A), the treatment is initiated (FIG. 7B), and embolized material 734 is captured in the filter 100 (FIG. 7C). Thereafter, the debris 734 is removed prior to filter recapture or, alternatively, with treatment in the filter 100 via a sheath as previously described. The device 100 is recovered into the sheath (FIG. 7D) and removed from the lumen 10 (FIG. 7E).

Figure 8A:
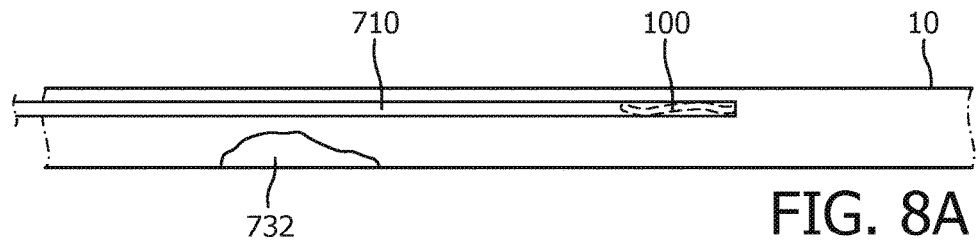
Figure 8B:
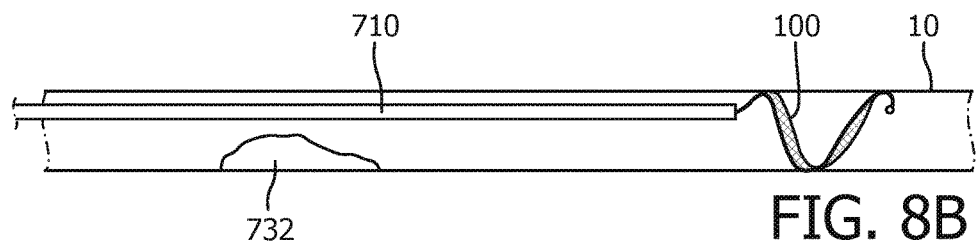
Figure 8C:
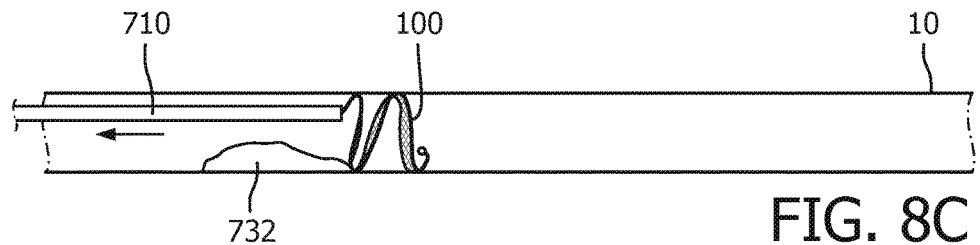
Figure 8D:
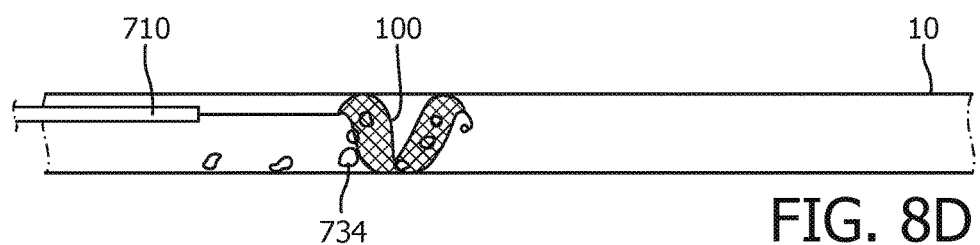
Figure 8E:
Figure 8F:
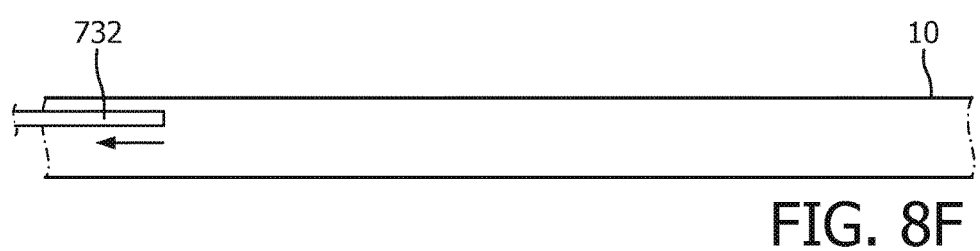

A tethered device (FIG. 7A, 8A) can also be employed to mechanically dislodge and remove embolic material 732 from a vessel 10, such as in the case of a thrombectomy. This offers a simple means of removing and trapping debris without requiring multiple devices to achieve the same goal. For this method, the tethered device is advanced downstream of the lesion site (FIG. 8A), and deployed (FIG. 8B). The tethered, deployed filter 100 is then drawn across the lesion 732 (FIG. 8C) to pull the thrombus from the vessel wall and into the filter 100 (FIG. 8D). The embolized material 734 is then removed via the methods previously described (FIG. 8E), tethered device is drawn into the sheath and removed from the lumen (FIG. 8F).

In some embodiments, as illustrated in the FIGS. 9A-9B, the distal protection device or system 900 can include two filters, a proximal filter 902 and a distal filter 904. In other embodiments, more than two filters can be used. In some embodiments, the two filters can be independently tethered to a delivery device, which can be a tube or sheath with a guide wire lumen or simply a wire, while not being tethered to each other. In some embodiments, the filters are tethered directly, i.e. are attached directly, to the delivery device. In some embodiments, such a configuration allows the distance or length between the two filters to be independently adjusted by the user by manipulating a separate hub for each filter. In addition, in some embodiments the filters can be independently oriented within a vessel by rotating the filters using a corresponding portion of the hub. For example, rotating the corresponding portion of the hub can cause the filter to rotate in a similar manner. In general, the opening of the filter is oriented to face the direction of blood flow such that blood and any debris, such as emboli, plaque fragments, calcium deposits and/or other mineral deposits, in the blood flows into the opening of the filter and into the material capture structure.

In some embodiments, the proximal filter 902 can be tethered or attached to a first sheath 906 and the distal filter 904 can be tethered or attached to a second sheath 908 that is coaxial with the first sheath 906. In some embodiments, the second sheath 908 is disposed within the first sheath 906 and extends past the distal end of the first sheath 906. This double sheath design allows each filter to be independently manipulated by manipulation of the corresponding sheath on which the filter is attached. In some embodiments, the sheaths can be braid or coil reinforced to reduce kinking. In some embodiments, the first and second sheaths can be microcatheters. In addition, the double sheath design allows the distance between the two filters to be adjusted, which allows the filters to be properly placed in the brachiocephalic trunk and the left common carotid artery. Because the distance and anatomy between the left common carotid artery and the brachiocephalic trunk is highly variable between patients, it is very helpful to be able to adjust the distance between the filters to maintain wall apposition.

In addition, in some embodiments the first and second sheaths are disposed within an outer sheath 910. In some embodiments, the outer sheath 910 can be advanced over both the first and second sheaths 906, 908 to effect capture of the attached filters 902, 904. In some embodiments, the outer sheath 910 can have a curved, deflecting, steerable distal tip portion 912 adapted to aid in navigating the curvature of the vasculature. In some embodiments, the curvature of the distal tip portion 912 can be between about 10 to 60 degrees, or between about 20 to 45 degrees, or be about 15, 20, 25, 30, 35, 40, or 45 degrees.

In some embodiments, a stop 914 is provided between the filters. In some embodiments, the stop 924 is located on the second sheath 908 at a predetermined distance proximal of the distal filter 904, which can be located on or proximal the distal end of the second sheath 908. The stop 924 can be an enlarged section of the second sheath 908, such as a thick band or other raised structure that cannot be retracted within the lumen of the first sheath 906. Therefore, the stop 924 can provide a minimum separation distance between the two filters to prevent collisions and entanglements between the two filters during the deployment or removal/recovery phases.

In some embodiments, the sheaths can be over-the-wire type sheaths and can be advanced over a guidewire 926. In other embodiments, the smaller diameter second sheath 908 with the distal filter 904 can have a rapid exchange type guidewire lumen located on the distal portion of the sheath to allow the second sheath to be exchanged in a rapid exchange type manner (not shown).

In some embodiments, the distal end of the second sheath 908 can have an atraumatic tip 928 to prevent accidental puncture of the vessel wall and to atraumatically advance the sheath.

Figure 9C:
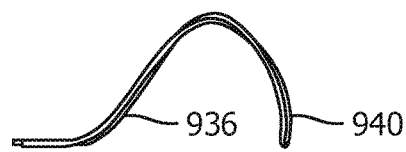
FIGS. 9C and 9D illustrate an embodiment of the frame of a distal protection filter.
Figure 9D:
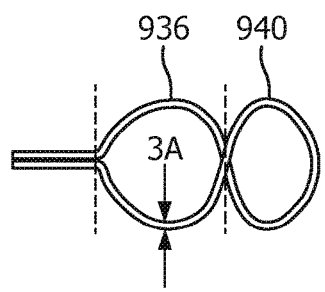
Figure 9E:
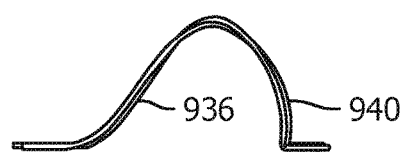
FIGS. 9E and 9F illustrate another embodiment of the frame of a distal protection filter.
Figure 9F:
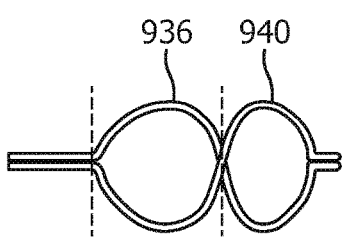
Figure 10A:
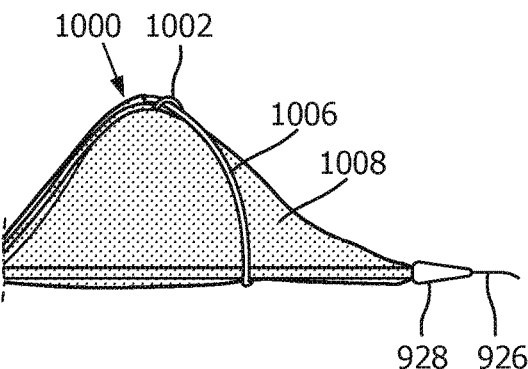
FIGS. 10A-10F illustrate an embodiment of a gap reducing feature on a distal protection filter.
Figure 10B:
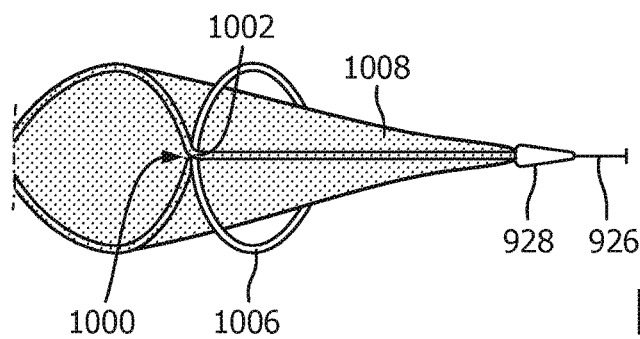
Figure 10C:
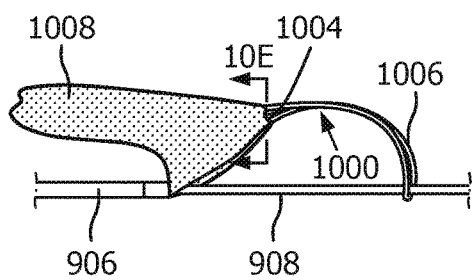
Figure 10D:
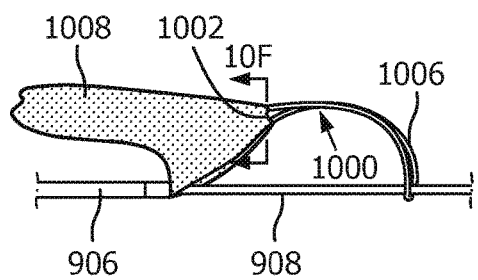
Figure 10E:
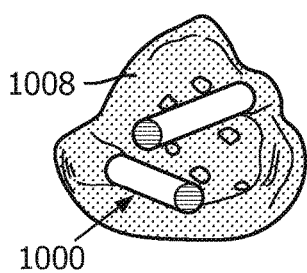
Figure 10F:
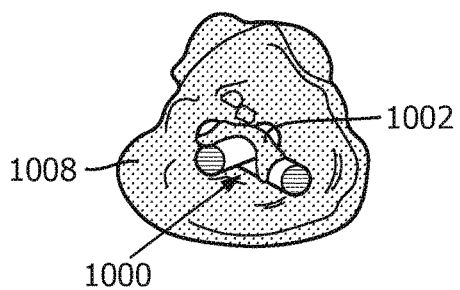

In some embodiments, the proximal filter 902 and the distal filter 904 can be made from a frame 932, 934 having a proximal loop 936, 938, a distal loop 940, 942 and a slidable crossover point 944, 946 between the two loops, and a material capture structure 948, 950 attached to one of the loops two loops. In some embodiments, the sheaths pass through the interior of the loops. In some embodiments as illustrated in FIGS. 9C and 9D, the frame can be formed from a single wire or structural element that is oriented in a figure eight configuration. In some embodiments, the slidable crossover point is offset from an axis that connects the proximal end and the distal end of the frame. This offset can define the height of the filter structure. In some embodiments, the two ends of the single wire frame can be attached to one of the sheaths of the device by a fastener 952, 954 such that the sheath is located within the loop. In some embodiments as illustrated in FIGS. 9E and 9F, the frame can be formed from two wires or structural elements with opposing spirals that form a figure eight structure with a slidable crossover point that is offset from an axis that connects the proximal end and the distal ends of the frame.

In some embodiments, the proximal filter 902 can have an orientation with an opening 956 that faces towards the distal end of the device 900 and can have a material capture structure 948 attached to the trailing edge or proximal loop 936 of the proximal filter structure, while the distal filter 904 can have an orientation with an opening 958 that faces towards the proximal end of the device 900 and can have a material capture structure 950 attached to the leading edge or proximal loop 938 of the filter structure. In some embodiments, the material capture structure is attached to the proximal edge or loop of each filter.

In some embodiments, the material capture structure is pleated to accommodate the movement of the elongate members and crossover point while maintaining emboli and debris protection across the entire cross-sectional area of the lumen. In some embodiments, the material capture structure can have one or more pleats located adjacent or near the crossover point. In some embodiments, the material capture structure can have an overlapping portion at the crossover point that functions similarly to the pleat to provide material capture structure coverage in the event of separation of the elongate members at the crossover point. In some embodiments, as illustrated in FIGS. 10A-10F, the crossover point 1000 can include a crossover loop 1002 or some other restraining feature that keeps the elements of the frame that form the crosspoint point 1000 in substantial apposition or contact while still allowing the crossover elements to slide against one another. Like the pleat, the crossover loop 1002 prevents or reduces the gap 1004 that can form in between the frame 1006 and the material capture structure 1008 when the frame elements separate from one another. Such a gap may allow embolic debris to leak through the filter. Therefore, preventing or reducing the gap 1004, by for example providing additional material capture structure in the form of a pleat or by preventing or reducing the separation of the frame elements at the crossover point, can improve the capture efficiency of the filter.

Figure 11A:
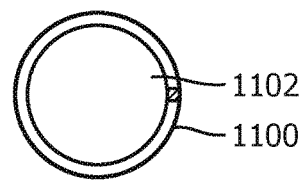
FIGS. 11A and 11B illustrate an embodiment of the construction of a frame element.
Figure 11B:
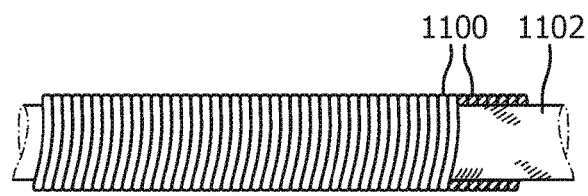

In some embodiments, as illustrated in FIG. 9A, radiopaque markers 930 can be provided on the sheaths and/or filters in order to visualize the location of the sheaths and filters during the delivery and recovery process. In some embodiments, the radiopaque marker 903 can be discrete bands incorporated in the sheaths and/or filters. In other embodiments, the sheaths and/or filters can include a coil of radiopaque wire or ribbon, such as platinum wire or ribbon, that can be incorporated into the sheaths and/or filters, making entire portions of the sheaths and/or filter radiopaque. For example, as illustrated in FIGS. 11A and 11B, a radiopaque wire or ribbon 1100 can be wrapped around a superelastic shape memory metal wire or frame core 1102, made from Nitinol for example, to form the filter frame. Similarly, a radiopaque wire or ribbon 1100 can be wrapped around distal portions of the sheaths were visualization is desired. The wrapped radiopaque wire or ribbon can also provide an irregular surface that facilitates attachment of the filter membrane to the filter frame.

Figure 11C:
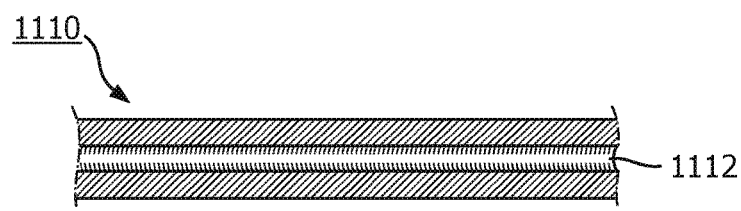
FIG. 11C illustrates a side cross-sectional view of an embodiment of a sheath.
Figure 11D:
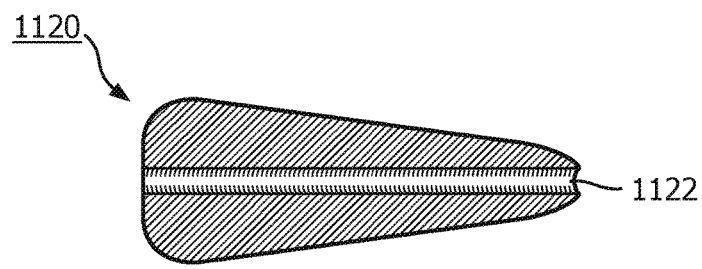
FIG. 11D illustrates a side cross-sectional view of an embodiment of an atraumatic tip.

FIGS. 11C and 11D illustrate close up cross-sectional views of a sheath 1110 and the atraumatic tip 1120. The sheath 1110 has a lumen 1112 that can receive a guidewire or another sheath. Similarly, the atraumatic tip 1120 has a lumen 1122 that can receive a guidewire.

In some embodiments, the end of the filter with the material capture structure, such as the loop in which the material capture structure is attached, can be tethered or attached to the delivery device, while the end of the filter without the material capture structure, such as the loop that is not attached to the material capture structure, can remain free. In some embodiments, tethering only one end of the filter to the delivery device allows the filter greater flexibility in its deployed orientation with respect to the orientation of the delivery device, which can improve the seal or fit of the filter within the vessel. In some embodiments, both ends of the filter can be tethered to the delivery device. In some embodiments, the end of the filter without the material capture structure can be tethered to the delivery device. In some embodiments, the openings of the two filters face each other. In some embodiments, the opening of the two filters face in the same direction, which can be either towards the distal end of the filter or the proximal end of the filter. In some embodiments, the openings of the two filters face away from each other.

As illustrated in FIGS. 12A-12E, in some embodiments each filter 1200 can be attached to an outer sheath 1202 and an inner sheath 1204, such that the proximal loop 1206 is attached to the outer sheath 1202 and the distal loop 1208 is attached to the inner sheath 1204. This configuration allows longitudinal length and compression of the filter 1200 to be controlled by the user by manipulating a hub at the proximal end of the sheath or by manipulating the proximal end of the sheath directly. By decreasing the filter length, the height of the filter 1200 is increased allowing the filter to provide complete or substantial wall apposition in a larger diameter vessel, as shown in FIG. 12B. The slidable crossover point allows the filter to dynamically adapt to the shape of the anatomy. Once the desired filter length or height is obtained, a locking mechanism 1210, such as a Touhy-Borst lock or ratchet lock or the like which can be incorporated into or with the hub portions, can be used to lock the outer sheath 1202 to the inner sheath 1204 to fix the filter dimensions. A locking mechanism 1210 can also be used in other embodiments described herein, by for example incorporation with the hub and hub portions illustrated in FIG. 20, to lock the position of one sheath to another sheath or to the guidewire. Similarly, by increasing the filter length, the height of the filter 1200 is decreased allowing the filter to more easily provide complete or substantial wall apposition in a smaller diameter vessel, as shown in FIG. 12C. As illustrated in FIGS. 12D and 12E, the height of the filter, including the size of each individual loop, can be customized by manipulating the telescoping sheath to increase or decrease the length of the filter, where the height of the filter or individual loop is inversely related to the length of the filter or individual loop.

In some embodiments, the material capture structure, which can be conical for example, can be formed from a flat filter membrane or film sheet. The filter sheet can be cut and folded into the desired shape, such as a cone for example, and the seam can be thermally bonded, mechanically stitched together, or bonded together at the surface using an adhesive. In some embodiments as illustrated in FIGS. 13A-13C, the filter sheet 1300 can be attached to a loop on the filter frame 1302 by stitching with a biocompatible thread or suture, by adhesive bonding, or by thermal bonding. In some embodiments, a portion of the mouth of filter sheet 1300 can be folded over the loop on the filter frame 1302 before attachment 1304.

In some embodiments, the material capture structure 1400 contains a number of filter cells or pores 1402, as illustrated in FIG. 14A-14B. Filter cells or pores may be formed in a number of different ways and have a number of different shapes and sizes. The shape, size and number of filter cells or pores in a specific filter may be selected based on the use of a particular filter. For example, a filter device of the present invention configured for distal protection may have a filter cell size or pore size on the order of tens to hundreds of microns to less than 5 millimeters, or less than or equal to about 1000, 900, 800, 700, 600, 500, 400, 300, 200, 100, 90, 80, 70, 60 or 50 microns. In some embodiments, the filter cell size or pore size is formed by a selecting a filter material with a cell size or pore size suited to the desired filtration level. In some embodiments, the filter material can be a polymer membrane or film or mesh. The polymer can be polyurethane, polyethylene, nylon or the like. The polymer membrane can be between about 0.5 to 3 mil thick, or about 0.75 to 1.5 mil thick, or about 0.5, 1.0, 1.5, or 2.0 mil thick. Using a thin membrane allows the filter membrane to be easily collapsed or folded into a delivery catheter and also facilitates retrieval back into the catheter.

In some embodiments, the pores are laser drilled into the membrane. In some embodiments, the filter cells are formed from a mesh. In some embodiments, the pore size, shape, density, orientation, and distribution on the membrane can be adjusted to control the flow rate profile through the filter membrane. For example, in some embodiments, the shape of the pore can be circular, ellipsoid, oval or oblong. In a conical filter for example, an oval pore with its major axis aligned with the filter axis can present a more circular cross-sectional opening when viewed along the longitudinal axis. In addition, the pore distribution can be adjusted to provide higher pore density and/or larger pores at or near the periphery of the membrane, which is generally adjacent to the blood vessel wall after implantation. In some embodiments, the pores can be ellipsoid, oval or oblong towards the periphery of the membrane. For example as illustrated in FIG. 14B, the peripheral portions 1404 of the filter membrane that resides at or near the periphery of the blood vessel lumen can have a greater pore density and/or greater pore size than the central portions 1406 of the filter membrane that resides in the central portion of the vessel lumen. This configuration provides increased debris protection for the central portion of the filter membrane, which tends to receive debris that can be deflected from the periphery toward a central holding zone of, for example, a conical filter. As debris fills the central holding zone, the central portion of the membrane can become clogged or blocked, which can reduce or stop flow of blood through the central portion of the membrane. To compensate for the blocked central portion, the peripheral portions of the membrane can have larger pores and/or a higher pore density in order to allow a sufficient amount of blood through the debris filled filter membrane.

In some embodiments, the filter membrane has an open area between 25 to 75 percent, or between about 33 to 66 percent, or between about 40 to 60 percent, or about or at least about 35, 40, 45, 50, 55, 57, 60 or 65 percent, where the open area refers to the area occupied by the pores. Sufficient open space is important to allow an adequate flow of blood through the filter membrane and to the brain, if used to protect the neurovasculature. In some embodiments, a contrast dye or radiopaque fluid can be introduced upstream of a deployed filter to determine whether the filter membrane is occluded and the degree of occlusion. In some embodiments, the contrast dye or radiopaque fluid can be delivered through a lumen and fluid delivery port in the distal filter delivery device. In other embodiments, the contrast dye or radiopaque fluid can be delivered by a separate catheter.

Figure 15A:
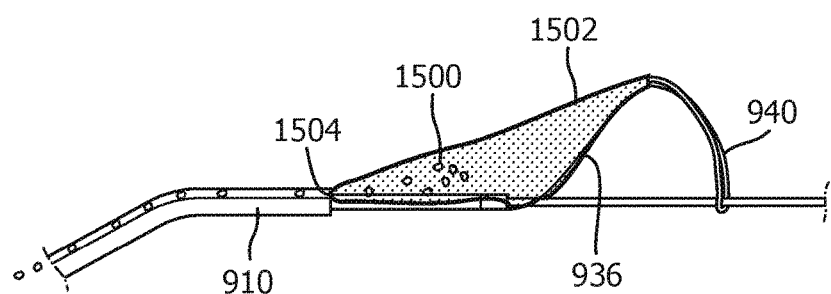
FIGS. 15A and 15B illustrate embodiments of a filter device with a built-in aspiration mechanism.
Figure 15B:
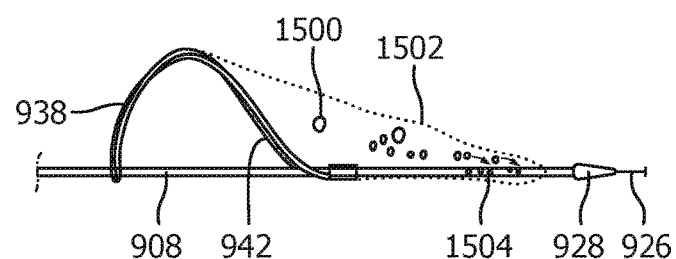

In some embodiments as illustrated in FIGS. 15A and 15B, the embolic debris 1500 can be aspirated from the material capture structure 1502 using an aspiration port 1504 included with the filter device. In some embodiments, the aspiration port 1504 can be located at or near the apex of the material capture structure 1502 where the debris 1500 is generally funneled to. In some embodiments, the aspiration port 1504 can be located on the distal end of a sheath which is connected to the apex of the material capture structure 1502. In other embodiments, the aspiration port 1504 can be located along the length of the sheath on which the material capture structure 1502 is attached. In some embodiments, one or more aspiration ports 1504 are used to aspirate the debris. In some embodiments, a separate aspiration catheter can be used to aspirate debris 1500 from the material capture structure 1502.

In some embodiments, the material capture structure, filter membrane or mesh can be coated with an anticoagulant such as heparin. In some embodiments, the other portions of the device in contact with blood, such as the catheter and tether and filter frame, can be coated with an anticoagulant. In some embodiments, the filter and/or filter membrane or mesh can be coated with a drug or pharmaceutical compound.

In some embodiments, the frame of the filter does not have any additional anchoring structures that penetrate into the vessel wall. The force exerted by the self expanding frame against the vessel wall along with the attachment of the filter to the delivery sheath during the entire procedure can provide sufficient stability to the filter and prevent substantial migration of the filter during the procedure. Relative to the venous vessels such as the vena cava, the arterial vessels are less compliant and can undergo less change in diameter over time. This makes it less necessary to provide relatively invasive fixation means. In some embodiments, the frame of the filter can include one or more anchors that do not penetrate completely through the vessel wall. In the branch arteries off the aorta, puncture through the vessel wall may lead to excessive bleeding or rupture. Therefore, in some embodiments, the anchors can be sized and designed to penetrate only part way through the vessel wall. For example, the anchors can extend radially outwards for a distance that is less than the thickness of the vessel wall, which can be less than about 0.75, 0.5, or 0.25 times the thickness of the vessel wall. In other embodiments, the anchors are designed to engage the vessel wall in an atraumatic manner.

Figure 16:
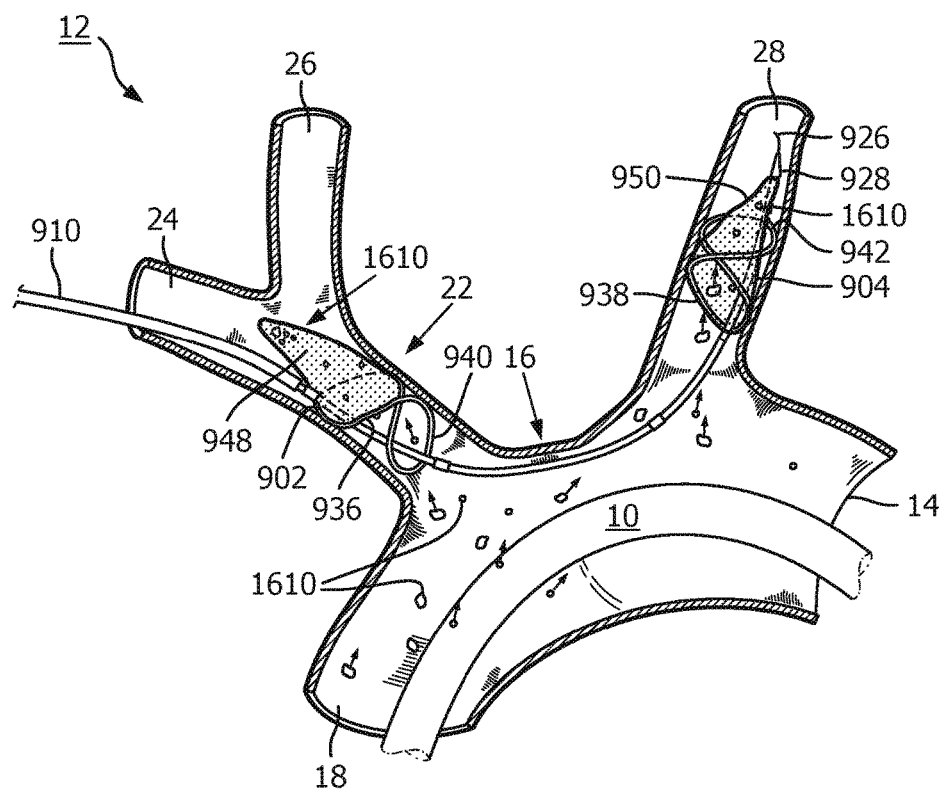
FIG. 16 illustrates an embodiment of the filtering device with a distal protection filter deployed in the left common carotid artery and another distal protection filter deployed in the brachiocephalic trunk.
Figure 17A:
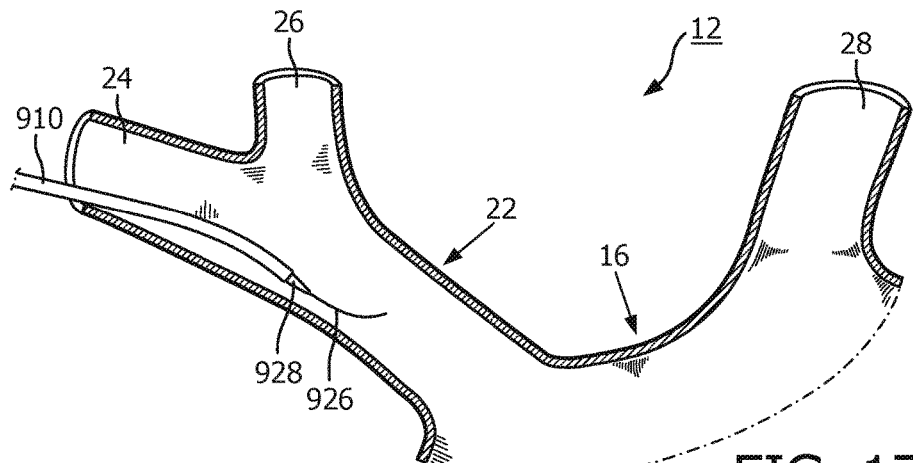
FIGS. 17A-17L illustrate an embodiment of a method of deploying distal protection filters to two arteries.
Figure 17B:
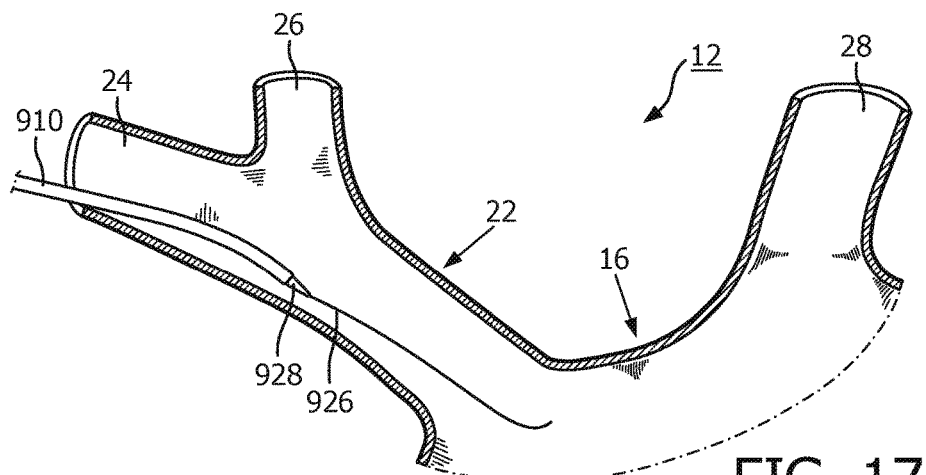
Figure 17C:
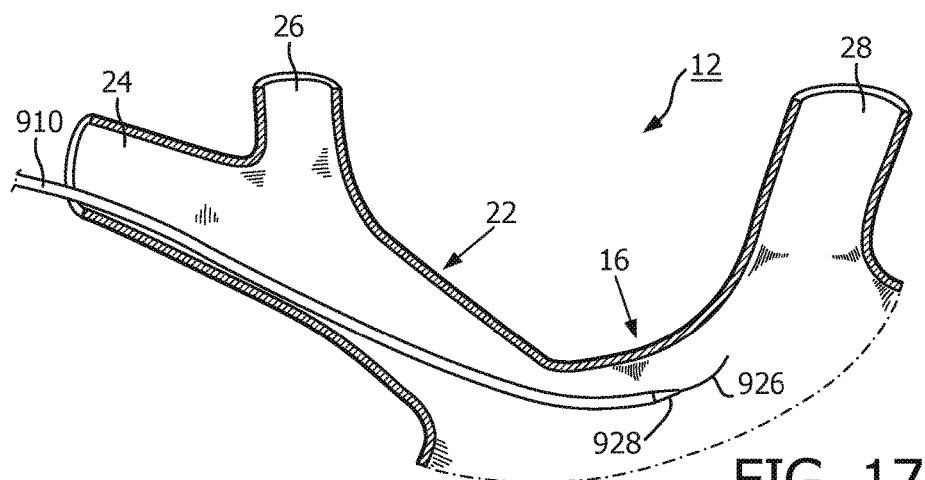
Figure 17D:
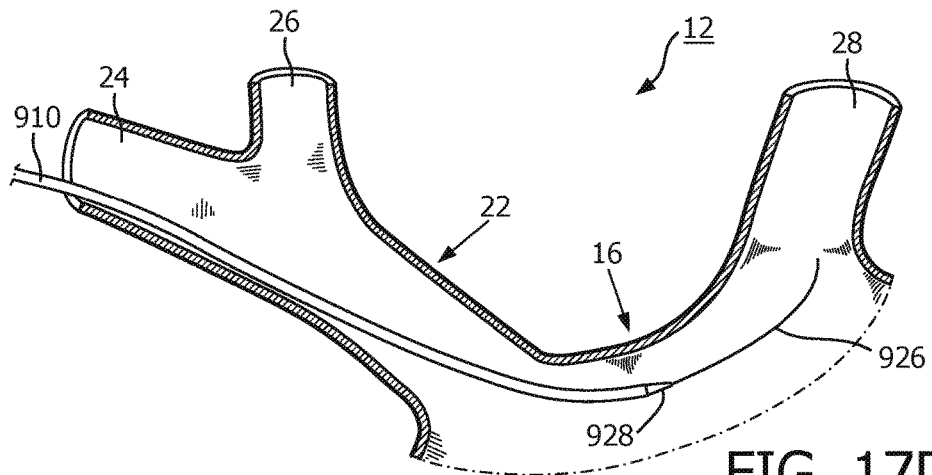
Figure 17E:
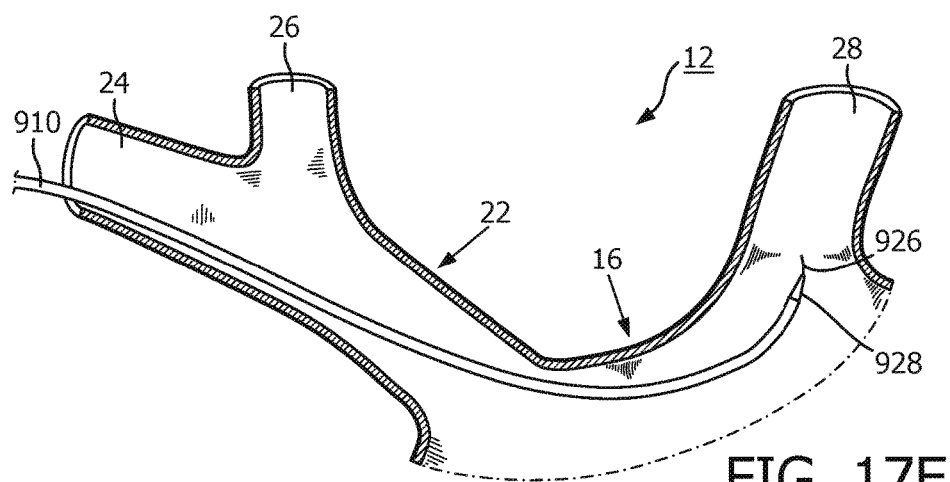
Figure 17F:
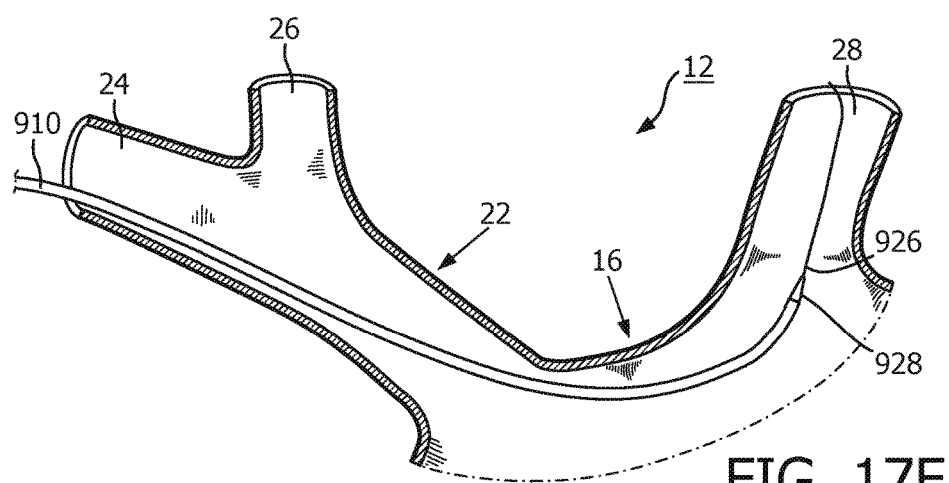
Figure 17G:
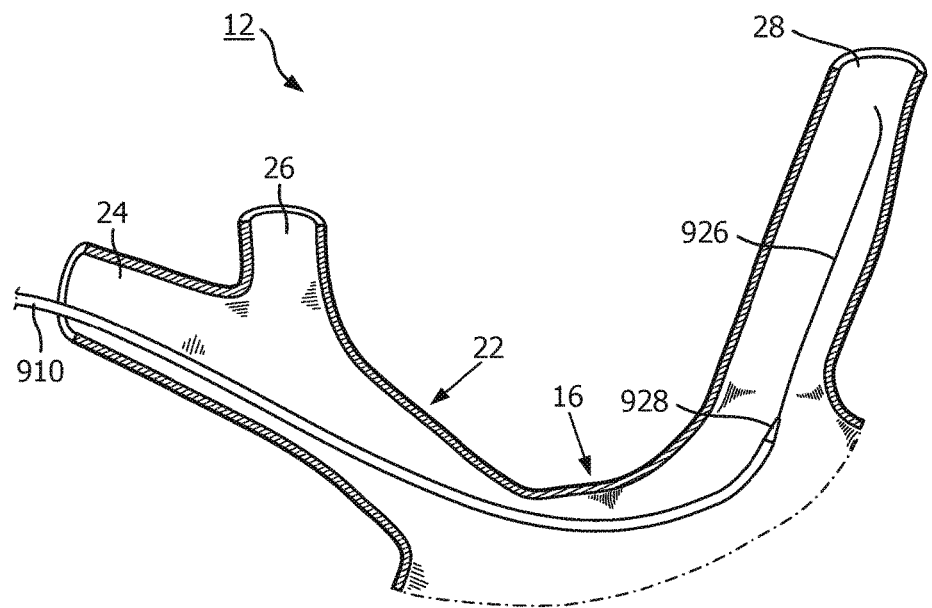
Figure 17H:
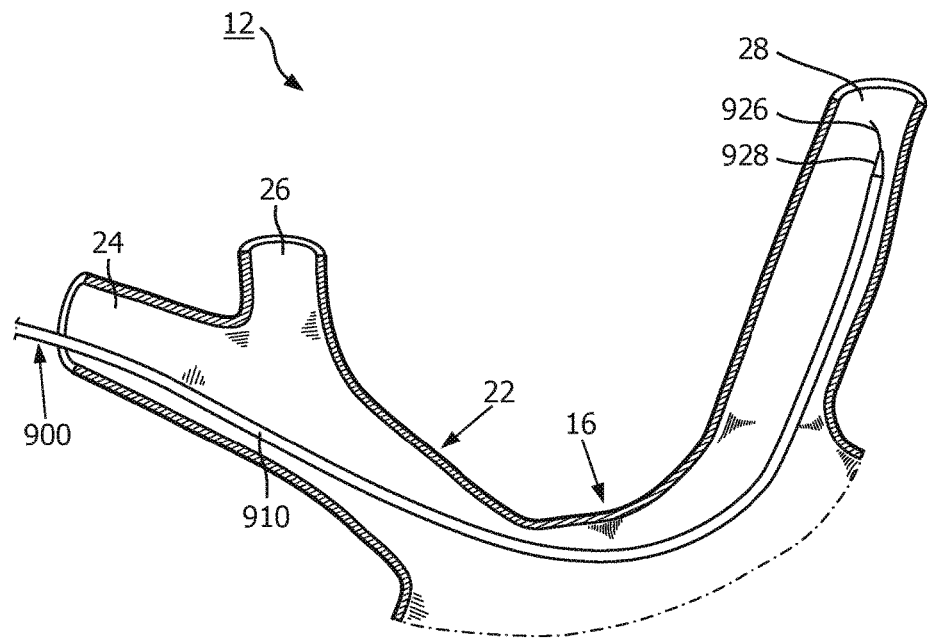
Figure 17I:
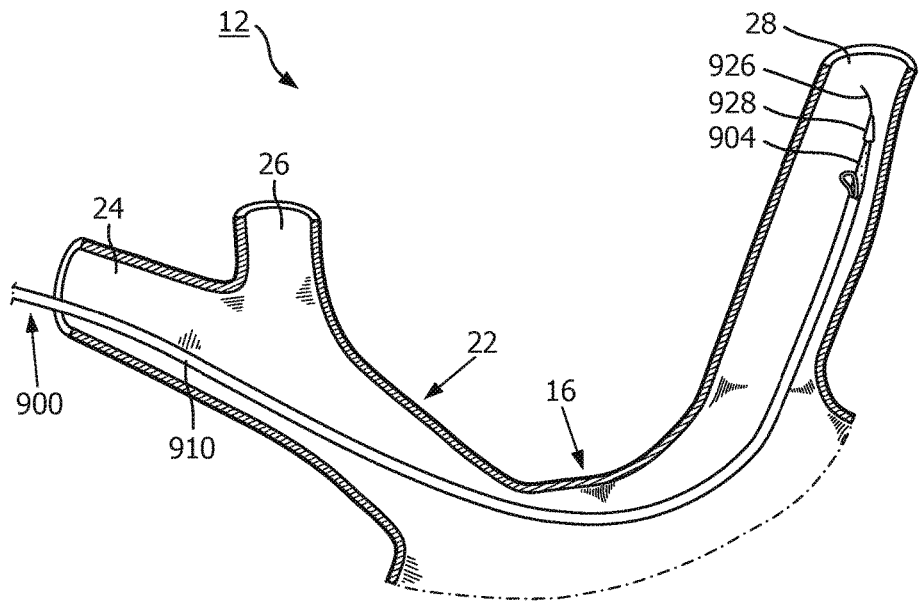
Figure 17J:
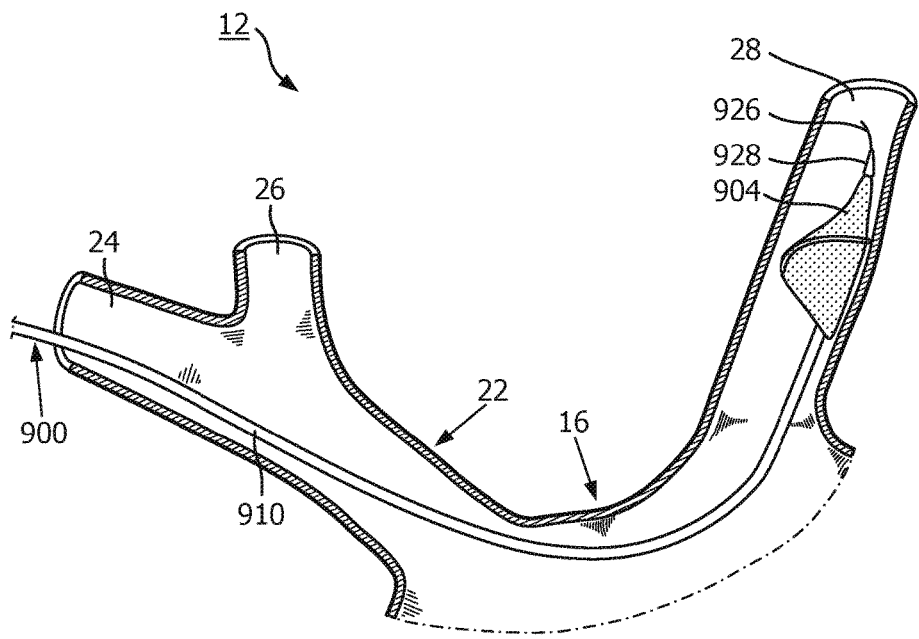
Figure 17K:
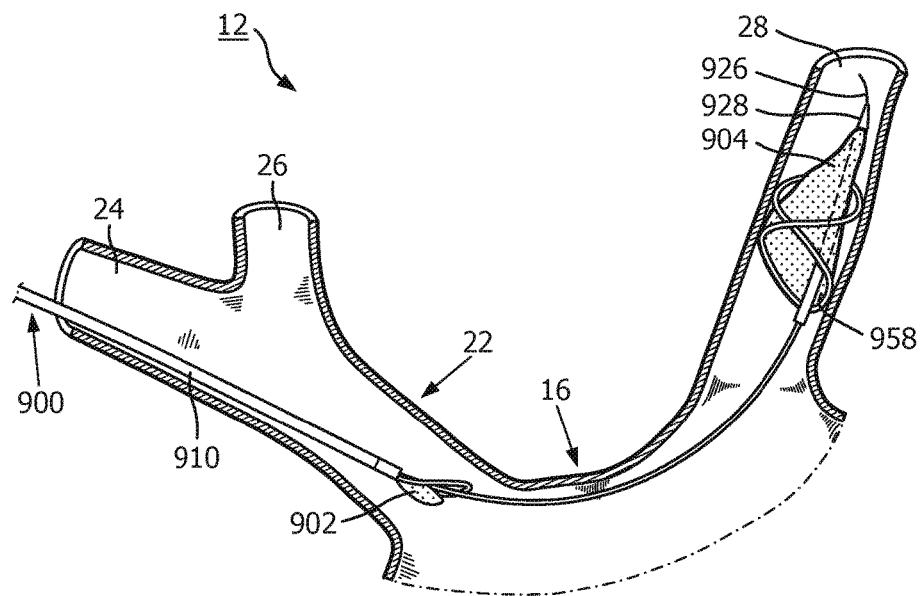
Figure 17L:
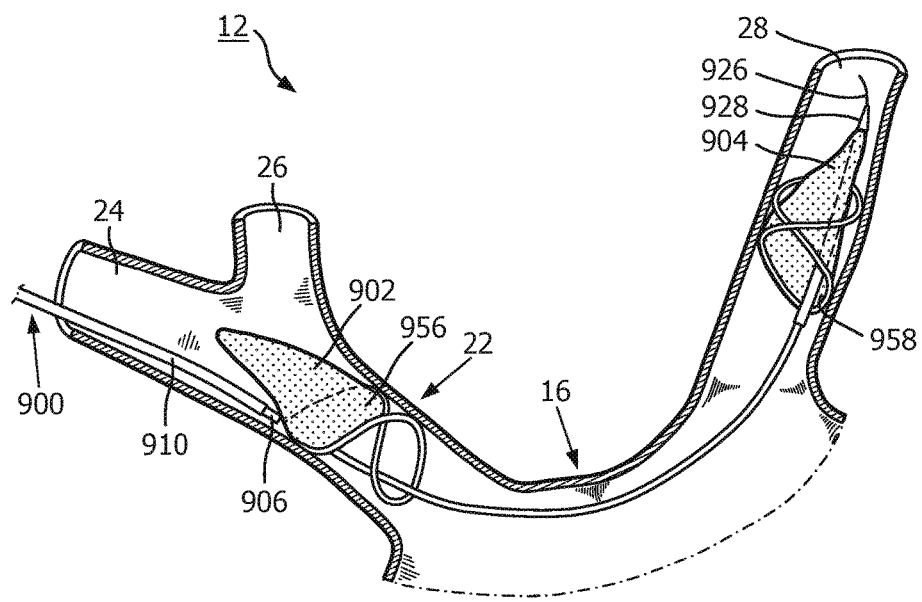

In some embodiments as illustrated in FIG. 16, the dual filter configuration allows the user to place one filter 902 in a first location in the vasculature, such as in the brachiocephalic trunk 22, and the second filter 904 can be placed in a second location in the vasculature, such as a portion of the left common carotid artery 28 that branches off the aorta 12. In some embodiments, a filter can also be placed in the left subclavian artery (not shown). In some embodiments, the goal is to provide protection of the neurovasculature by protecting the left and right common carotid artery 26, 28. Placement of filters in both the brachiocephalic trunk 22 and the left common carotid artery 28 provides emboli and debris protection for the arteries that supply blood to the brain, where emboli or debris 1610 can cause severe adverse events such as stroke. By preventing procedure related emboli and debris 1610 from reaching the neurovasculature, the risk of stroke can be reduced.

In other embodiments, the filters can be placed in other vessels branching off the aorta, such as the left subclavian artery, the right and left coronary artery, the mesenteric arteries and the renal arteries. In some embodiments, one or more of the filters can be deployed in the vasculature according to the configurations disclosed in U.S. Pat. No. 6,485,502 to Don Michael et al., U.S. Pat. No. 7,806,906 to Don Michael, U.S. Publication No. 2006/0100658 to Obana et al., and U.S. Publication No. 2008/0004687 to Barbut et al., which are hereby incorporated by reference in their entireties.

In some embodiments, the distal filter 904 can be placed first at the second location, such as the left common carotid artery 28, and then the proximal filter 902 can be retracted to the first location, such as the brachiocephalic trunk 22, and placed next. In some embodiments, the filter delivery device can access the first location and/or the second location through one of the arteries that branches off the aortic arch 16, such as the brachiocephalic trunk 22, the left common carotid artery 28 or the left subclavian artery, for example. In other embodiments, the proximal filter 902 can be placed first at the first location and then the distal filter can be advanced to the second location and placed next.

In some embodiments as illustrated in FIGS. 17A-17L, filters can be introduced into a patient's blood vessels as follows. In some embodiments as illustrated in FIGS. 17A-17G, a guidewire 926 can be introduced into a peripheral artery, such as the right brachial or radial artery, and then advanced into the right subclavian artery 24. From the right subclavian artery 24, the guidewire 926 can be further advanced into the brachiocephalic trunk 22, then into the aortic arch 16 of the aorta 12, and then into the left common carotid artery 28. In other embodiments, the filters can be delivered to the left common carotid artery and brachiocephalic trunk through the femoral artery.

In some embodiments, a sheath can be optionally advanced over the guidewire to allow the guidewire to be exchanged for a stiffer guidewire. The stiffer guidewire may be better able to maintain its position in the left common carotid artery than a more flexible guidewire when the catheter or sheath carrying the filter is advanced over the guidewire. Because the catheter or sheath carrying the filter tends to be stiffer than the first, flexible guidewire, the operator can inadvertently dislodge the first guidewire from the left common carotid artery as the catheter or sheath carrying the filter is advanced into the aortic arch and is forced to make a bend towards the left common carotid artery. Increasing the stiffness of the guidewire with the stiffer second guidewire helps resist this dislocation force exerted by the filter catheter. In addition or alternatively, a sheath with an appropriately curved tip portion can be used to help steer the guidewire 926 through the vasculature. In some embodiments, the sheath can be the outer sheath 910 of the filter delivery device 900. In other embodiments, the sheath can be separate from the filter delivery device 900 and can be removed after the guidewire 926 has been placed into the left common carotid artery 28 or other target location, and then be replaced by the filter delivery device 900.

Once the guidewire 926 is in place in the left common carotid artery 28, the filter delivery device 900 can be introduced over the guidewire 926 and advanced to the left common carotid artery 28, where the filter deployment process can begin, as illustrated in FIGS. 17G-17L. More specifically, the filter delivery device 900, which includes the plurality of sheaths with attached filters as described above, can be introduced over the guidewire 926 and into the brachiocephalic trunk 22 and then advanced towards the aorta 12. The distal filter 904 can then be advanced into the aortic arch 16, while covered by the outer sheath 910, and into the left common carotid artery 28, where the distal filter 904 can be deployed by retracting the outer sheath 910 over the distal filter 904. As the outer sheath 910 is retracted over the distal filter 904, the distal filter 904 can self-expand to engage the left common carotid artery wall. The distal filter 904 is deployed such that the mouth 958 of the distal filter 904 resides within the left common carotid artery 28. Next, the first sheath 906, which is attached to the proximal filter 902, is manipulated such that the mouth 956 of the proximal filter 902 resides in the brachiocephalic trunk 22. This manipulation can be done within the outer sheath 910, and depending on the location of the proximal filter 902 after the distal filter 904 has be deployed, can require the proximal filter 902 to be retracted or advanced into the brachiocephalic trunk 22.

Once the proximal filter 902 is in place within the brachiocephalic trunk 22, the proximal filter 902 can be deployed from the delivery device 900 to reside in the brachiocephalic trunk 22 by retracting the outer sheath 910 over the proximal filter 902. As the outer sheath 910 is retracted over the proximal filter 902, the proximal filter 902 can self-expand to engage the brachiocephalic trunk wall. As illustrated in the FIGS. 9A and 17L, both filters have openings that face each other in the stowed configuration and when deployed face the aortic arch. Such a delivery method and device configuration reduces and/or minimizes the amount of the distal protection device that occupies the aorta, thereby reducing and/or minimizing any interference with the main operational procedure to be performed, such as a percutaneous aortic valve replacement.

The length of the spacing between the two filters, which can be adjusted using the stop feature, can have an effect on whether the proximal filter will need to be retracted or advanced into the correct location in the brachiocephalic trunk. In some embodiments, the spacing between the filters is relatively long such that after deployment of the distal filter, the proximal filter is resides within the brachiocephalic trunk. In some embodiments, the proximal filter may be then advanced into position such that the mouth of the proximal filter is located within desired location within the brachiocephalic trunk. In other embodiments, the spacing between the filters is relatively short such that after deployment of the distal filter, the proximal filter resides within the aortic arch, which means that the proximal filter can then be retracted into brachiocephalic trunk.

Figure 18A:
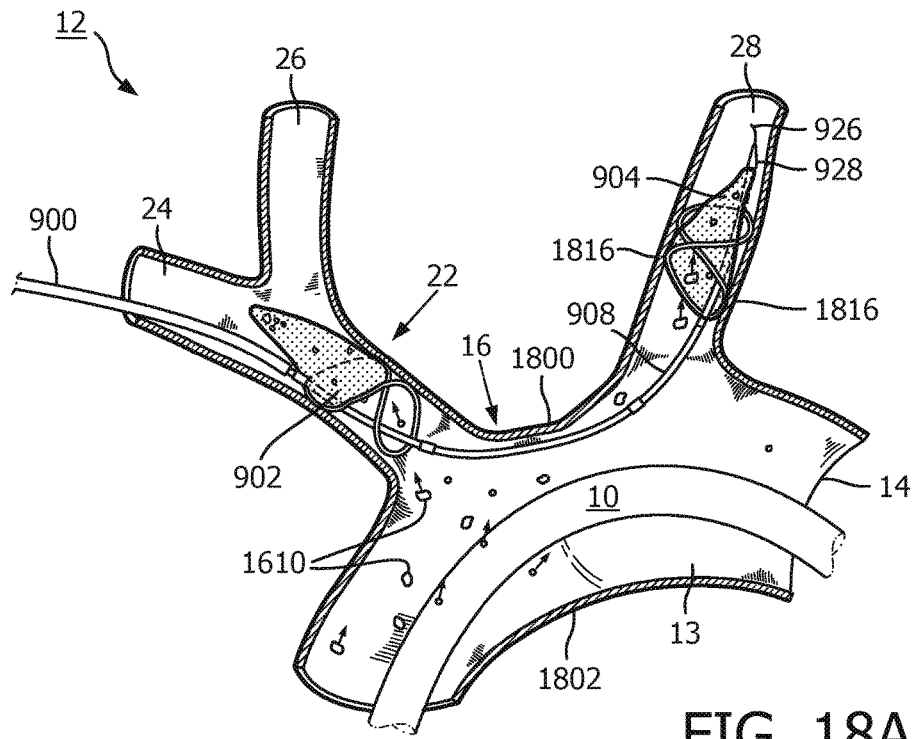
FIGS. 18A-18C illustrate embodiments of various orientations of the sheath within the aorta to minimize or reduce interference with a procedure catheter.

Furthermore, the spacing between the two filters can have an effect on the amount and/or the configuration of the sheath or catheter than remains in the aortic arch when the filters are in place. It can be important to minimize or reduce the obstruction of the aortic lumen by the sheath or catheter in order to minimize or reduce interference with subsequent surgical procedures, such as percutaneous aortic valve repair PAVR that require insertion of catheters and other medical devices through the aortic arch. Collision of the PAVR catheter with the sheath or catheter of the distal protection filter, can cause dislodgement of the filters and/or entanglement between the devices and/or otherwise interfere with the surgical procedure. Various embodiments of the system and method that minimize or reduce obstruction of the aortic lumen are illustrated in FIGS. 18A-18E. In some embodiments as illustrated in FIG. 18A, in order to minimize or reduce the obstruction of the aortic lumen 13 by the sheath 908 or catheter of the filter device 900, the sheath 908 or catheter portion between the proximal filter 902 and the distal filter 904 can be kept taut or under tension to minimize or reduce the length of the sheath 908 or catheter between the two filters. In this configuration, the sheath 908 or catheter tends to abut or conform to the top 1800 of the aortic arch 16, also referred to as the outer radius 1800 of the aortic arch 16, between the left common carotid artery 28 and the brachiocephalic trunk 22. In some embodiments, the frame of the proximal filter 902, the distal filter 904 and/or sheath 908 or catheter portion between the two filters can include one or more anchors or securement elements 1816 that helps secure the sheath 908 or catheter to the top portion of the aortic arch 16 by allowing the user to apply tension to the sheath 908 which and/or by using anchors 1816 to secure the sheath 908 to the outer radius 1800. The anchors 1816 can be configured to extend towards the aortic arch wall, or can be manipulated to face the aortic arch wall, so that the likelihood that the anchors 1816 interfere with the surgical procedure catheter 10 or device is minimized or reduced. In some embodiments, anchors 1816 can have relatively short length to ensure that the anchors do not puncture the wall of the aortic arch. In some embodiments where the sheath 908 has an anchor, anchors 1816 can be located on the portion of the sheath opposite the crossover point of the proximal filter 902 and/or the crossover point of the distal filter 904. In some embodiments, the filter device 900 can have a plurality of anchors 1816 located in any of the locations described herein.

Figure 18B:
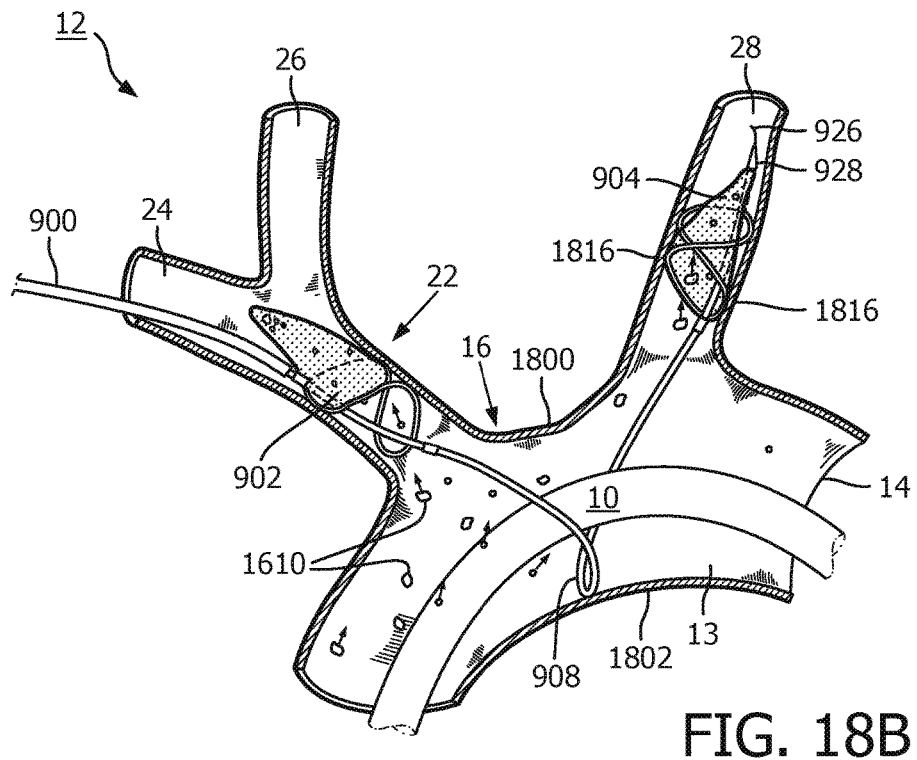
Figure 18C:
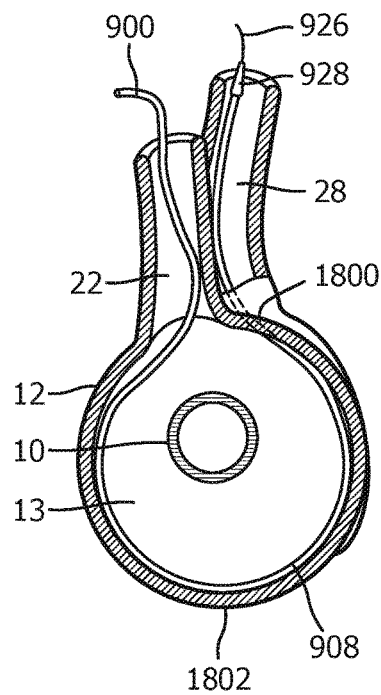

In other embodiments as illustrated in FIGS. 18B and 18C, the portion of the sheath 908 or catheter in the aortic arch 16 can extend downwards from the left common carotid artery 28, staying against inner wall the aortic arch and traversing from the outer radius 1800 of the aortic arch 16 proximate the left common carotid artery 28 to the inner radius 1802 of the aortic arch 16, before extending upwards towards the outer radius 1800 of the aortic arch 16 proximate the brachiocephalic trunk 22 and then into the brachiocephalic trunk 22, again staying against the aortic arch inner wall. This configuration results in a U shaped configuration for the sheath 908 or catheter while staying substantially out of the aortic arch lumen 13. In this embodiment, the distal filter 904 and/or sheath 908 or catheter can also have anchors 1816 as described above.

Figure 18D:
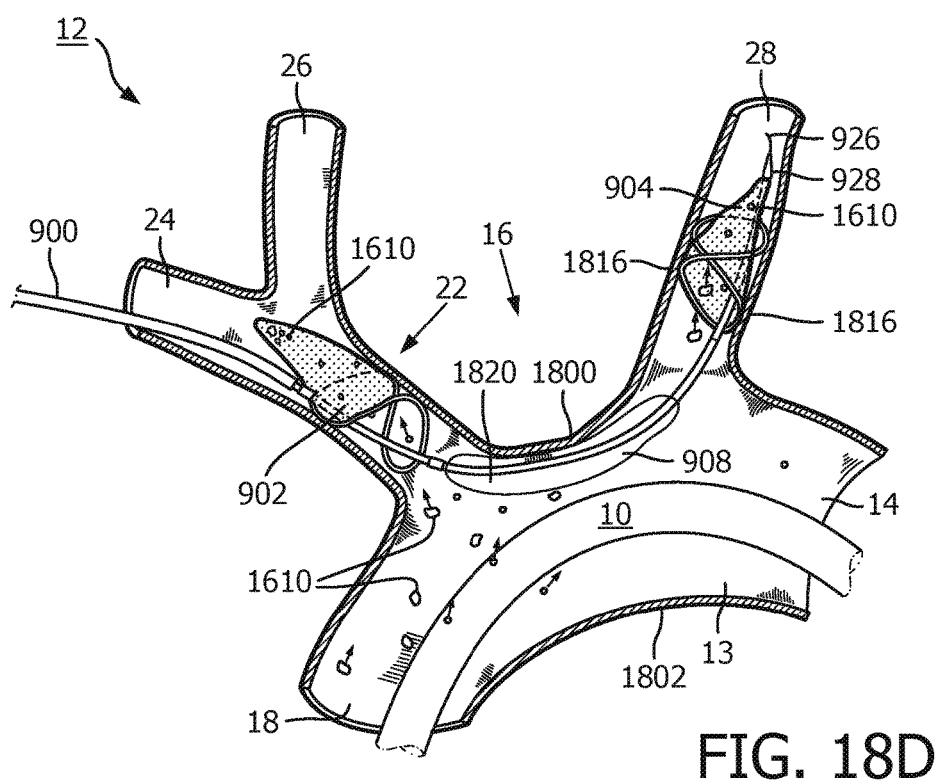
FIGS. 18D and 18E illustrate embodiments of various deflection mechanisms for deflecting a procedure catheter away from the filtering device.
Figure 18E:
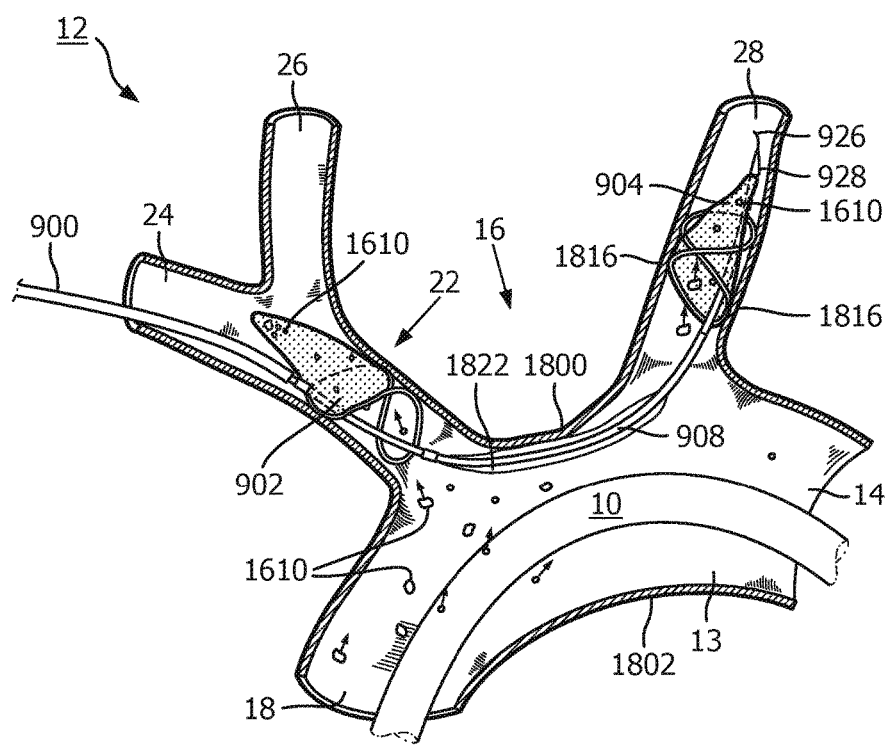

In other embodiments as illustrated in FIGS. 18D and 18E, which are modifications of the embodiment illustrated in FIG. 18A, a deflection mechanism can be incorporated on the portion of the sheath 908 or catheter between the two filters that resides against outer radius 1800 of the aortic arch 16. For example, FIG. 18D shows a balloon deflection mechanism 1820 that can be inflated after the filters are positioned in order to deflect the procedure catheter 10 from entanglement with the sheath 908 of the filter device 900. As the procedure catheter 10 is inserted into the aortic arch 16, it makes contact with the balloon deflection mechanism 1820 instead of the getting potentially entangled with the sheath 908. FIG. 18E shows various embodiments of the deflection mechanism, where a deflection shield 1822 is used in place of the balloon deflection mechanism 1820. The deflection shield 1822 can be flexible and flat and can be rolled up around the sheath 908 during delivery of the distal filter 904. As the outer sheath is further retracted, the deflection shield 1822 can be deployed and can unfurl into its flat configuration.

In other embodiments, the portion of the sheath 908 between the two filters can have a suture tether that allows the sheath 908 to be sutured against the aortic arch wall.

Figure 19D:
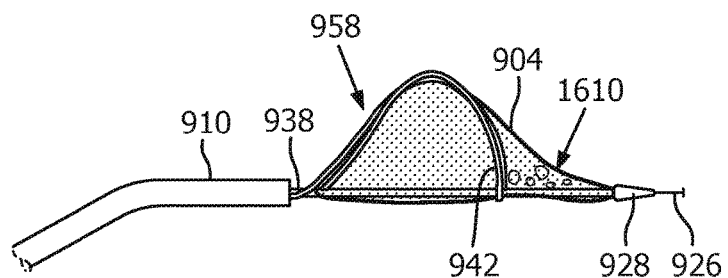
Figure 19E:
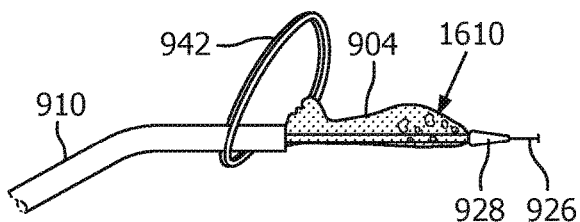
Figure 19F:
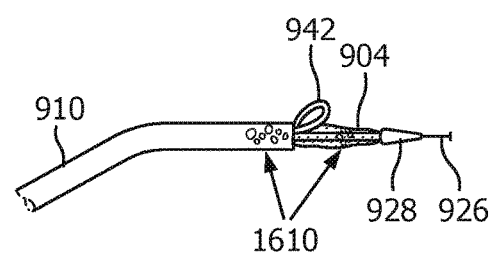

After completion of the main operation procedure, the process of removing the distal protection filters and any captured debris can be initiated, as illustrated in FIGS. 19A-19F. For example, in some embodiments, an outer sheath 910 can be advanced over the proximal filter 902 and the distal filter 904. As the outer sheath 910 is advanced over the first sheath 906, it first contacts the proximal edge or loop 936 of the proximal filter 902, which in some embodiments, also serves as the attachment for a material capture structure 948. As the outer sheath 910 is advanced over the proximal edge or loop 936 of the proximal filter 902, it causes the proximal edge or loop to collapse 936 and close the mouth or opening 956 of the material capture structure 948, thereby sealing the debris 1610 within the material capture structure 948 while not causing extrusion of the debris 160 out of the proximal filter 902. As explained above, this can occur because the apex 1916 of the material capture structure 948 is unattached to the first sheath 906. The outer sheath 910 can then be further advanced over the sealed off portion of the material capture structure 948 containing the trapped debris 1610 such that the apex 1916 is the last part of the material capture structure 948 to be encompassed by the outer sheath 910. In some embodiments, as shown in FIGS. 19B and 19E, the distal loop 940, 942 of the proximal filter 902 and/or the distal filter 904 can move proximally during the closure of the mouth of the material capture structure such that the distal loop can be proximal the crossover point during a portion of the mouth closure procedure. As the mouth closure procedure progresses, the distal loop can move distally such that the distal loop is again distal the crossover point before being completely withdrawn into the outer sheath. The outer sheath 910 can then be advanced over the second sheath 908 to the distal filter 904, where it first contacts the proximal edge or loop 938 of the distal filter 904, which in some embodiments also serves as the attachment for a material capture structure 950. Next, the outer sheath 910 can be advanced over the proximal edge or loop 938 of the distal filter 904 to close the opening 958 the material capture structure 950 to trap the debris 1610 within the material capture structure 950 without causing extrusion of the debris 1610 out of the distal filter 904. The outer sheath 910 can then be advanced over the sealed off portion of the material capture structure 950 of the distal filter 904 and the distal protection device and/or system can be removed from the patient.

Figure 20A:
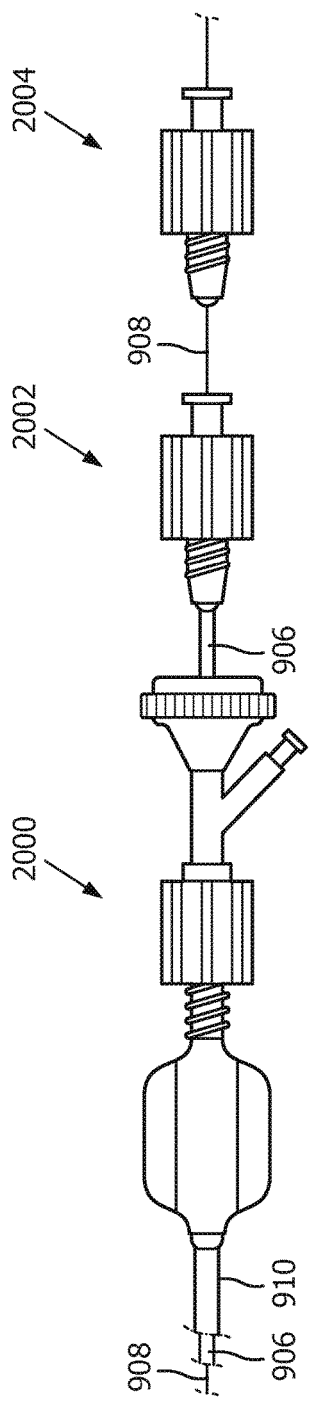
FIGS. 20A and 20B illustrate an embodiment of the various hubs used to manipulate the various components of the filtering device.
Figure 20B:
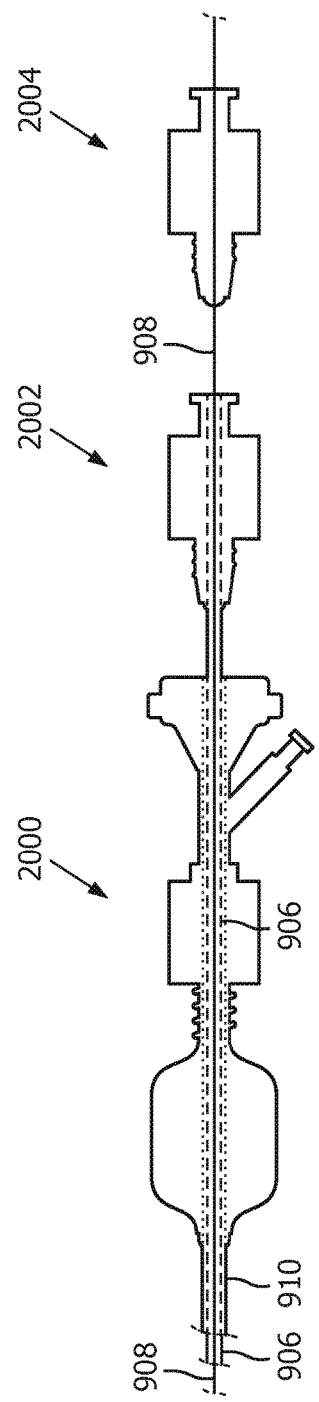

In some embodiments, the outer sheath of the distal protection device can be swapped out for a larger sheath or smaller sheath by removing the hub, then removing the original sheath, then inserting the new larger or smaller sheath, and then reattaching the hub. In some embodiments, the hub can be simply twisted off and twisted back on. The ability to swap out one sheath for a larger or smaller sheath can be useful for using the smallest sheath that is capable of enclosing the filter and the debris captured by the filter. However, if a large amount of debris is captured by the filter, it may be desirable to use a larger sheath to recover the filter, especially if the operator has difficulty or cannot advance the smaller sheath over the trapped debris. For example, FIG. 20 illustrates an embodiment of a plurality of removable hubs. There is an outer sheath hub 2000 that controls manipulation of the outer sheath 910, a proximal filter hub 2002 that controls the first sheath 906 and the proximal filter attached to the first sheath, and a distal filter hub 2004 that controls the second sheath 908 and the distal filter attached to the second sheath. Each of these hubs is detachable, which allows the outer sheath to be removed and replaced if desired. In some embodiments, the hubs can be lockable to lock the position of the sheaths. For example, one hub can be used to lock the position of the attached sheath while the other sheaths can be advanced or withdrawn, allowing the distance between the filters to be manipulated.

In some embodiments, the distal protection filters can be removed after the medical procedure is complete. In other embodiments, the distal protection filters can be left in for a predetermined amount of time before the filters are removed from the blood vessels. In some embodiments, the filters can be left in for up to 12, 24, 48, or 72 hours before removal. In some embodiments, a clogged filter can be swapped out with a new filter. In some embodiments, the filters can be left in the blood vessels to provide protection for up to 1 week, 2 weeks, 3 weeks, 4 weeks, 2 months, 3 months, 4 months, 5 months or 6 months when used in conjunction with periodic aspiration of the debris captured by the filters to prevent or reduce blockage of the blood flow through the filter. In some embodiments, the filters can be left in the blood vessel perioperatively, i.e. for the duration of the patient's surgical procedure, or sub-chronically, i.e. for a predetermined period of time postoperatively.

The distal protection filters described above can be used to capture debris that is generated by any medical procedure performed in the heart or circulatory systems, such as percutaneous aortic valve replacement (PAVR), transcatheter aortic valve implantation (TAVI), thoracic endovascular aortic repair (TEVAR), coronary artery bypass graft surgery (CABG), off-pump coronary artery bypass surgery (OP-CAB), mitral valve replacement (MVR), aortic valve replacement (AVR), left ventricle assist device, maze procedures, left ventricle catheterization, mitral valve procedure, electrophysiology (EP) ablation, closure of atrial septal defect (ASD), closure of patent foramen ovale (PFO), and closure of left atrial appendage (LAA).

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A system for providing embolic protection, the system comprising:
    a first sheath having a longitudinal axis, a proximal end, a distal end and a lumen, the lumen configured to receive a guidewire;
    a first distal protection filter attached to a distal portion of the first sheath, the first distal protection filter comprising a self-expanding frame with a slidable crossover point that defines a proximal loop and a distal loop, and a filter element attached to one of the proximal loop or distal loop of the self-expanding frame of the first distal protection filter, wherein the filter element extends to the crossover point;
    a second sheath disposed about the longitudinal axis and having a proximal end, a distal end and a lumen, the second sheath disposed over the first sheath, wherein the distal end of the second sheath is located proximally the first distal protection filter;
    a second distal protection filter attached to a distal portion of the second sheath, the second distal protection filter comprising a self-expanding frame with a slidable crossover point that defines a proximal loop and a distal loop, and a filter element attached to the proximal loop of the self-expanding frame of the second distal protection filter, wherein the crossover point is proximal to the filter element, wherein the proximal loops and the distal loops each includes a proximal end and a distal end; and
    an outer sheath disposed over both the first sheath and the second sheath; and
        wherein when deployed, the proximal loops, the distal loops, and the slidable crossover points of the first distal protection filter and the second distal protection filter are substantially positioned on a same side of a plane within which the longitudinal axis of the first sheath extends,
        wherein when deployed, the proximal ends of the proximal loops and the distal ends of the distal loops are substantially near the longitudinal axis, the distal ends of the proximal loops and the proximal ends of the distal loops at the crossover points are substantially away from the longitudinal axis.

2. The system of claim 1, wherein the filter element of the second distal protection filter has a mouth and an apex, wherein the mouth of the filter element is attached to the proximal loop and the apex is unattached to the second sheath.

3. The system of claim 1, wherein the first sheath includes a stop portion proximal the first distal protection filter, wherein the stop portion is configured to stop advancement of the second sheath proximal to the stop portion.

4. The system of claim 1, wherein in a stowed configuration within the outer sheath, the filter element of the first distal protection filter has a mouth facing the second distal protection filter and the filter element of the second distal protection filter has a mouth facing the first distal protection filter.

5. The system of claim 1, wherein the distance between the first distal protection filter and the second distal protection filter is adjustable.

6. The system of claim 5, wherein the position of the first sheath and the position of the second sheath are independently lockable, allowing one of the first sheath and the second sheath to be locked in position while the position of the other sheath is adjusted.

7. The system of claim 6, wherein the at least one anchor element of the first distal protection filter is configured to partially penetrate through the vessel wall.

8. The system of claim 1, wherein the self-expanding frame of the first distal protection filter includes at least one anchor element.

9. The system of claim 1, wherein the self-expanding frame of the second distal protection filter includes at least one anchor element.

10. The system of claim 1, wherein the first sheath includes at least one anchor proximal the first distal protection filter.

11. The system of claim 10, wherein the at least one anchor is located on a side of the first sheath opposite the crossover point of the first distal protection filter.

12. The system of claim 10, wherein the at least one anchor of the first sheath is configured to partially penetrate through the vessel wall.

13. The system of claim 1, wherein the filter elements of both the first distal protection filter and the second distal protection filter include a plurality of pores with a diameter of less than about 200 microns.

14. The system of claim 13, wherein the pores of the filter elements of both the first distal protection filter and the second distal protection filter are distributed more densely in the peripheral portion of the filter elements.

15. The system of claim 13, wherein the pores of the filter elements of both the first distal protection filter and the second distal protection filter are larger in the peripheral portion of the filter elements than in the central portion of the filter elements.

16. The system of claim 13, wherein the pores of the filter elements are oblong shaped.

17. The system of claim 1, wherein the filter elements comprises filter membranes with laser drilled holes.

18. The system of claim 1, wherein the filter elements comprise polymer fibers that are selected from the group consisting of electrospun fibers, knitted fibers, braided fibers, and woven fibers.

19. The system of claim 1, wherein the filter elements are made from a polymer selected from the group consisting of polyurethane, polyethylene, and nylon.

20. The system of claim 1, wherein the filter elements of both the first distal protection filter and the second distal protection filter have an open area between about 25 to 75 percent.

21. The system of claim 1, wherein the outer sheath is 9 Fr or less.

22. The system of claim 1, wherein the self-expanding frames of both the first distal protection filter and the second distal protection filter include a radiopaque marker.

23. The system of claim 22, wherein the radiopaque marker is a radiopaque coil of wire wrapped around a superelastic core.

24. The system of claim 1, the distal loops of both the first distal protection filter and the second distal protection filter are unattached to either the first sheath or second sheath.

25. The system of claim 1, wherein the outer sheath includes a curved distal portion with a curvature between about 15 to 45 degrees.

26. The system of claim 1, wherein the first distal protection filter and second distal protection filter are coated with a drug.

27. The system of claim 26, wherein the drug is heparin.

28. The system of claim 1, wherein the proximal loop of the first distal protection filter is attached to first sheath, and the proximal loop of the second distal protection filter is attached to the second sheath.

29. The system of claim 1, wherein the distal loop of the first distal protection filter is attached to first sheath, and the proximal loop of the second distal protection filter is attached to the second sheath.

30. The system of claim 1, wherein the self-expanding frame comprises a single wire element shaped in a figure eight configuration.

31. The system of claim 1, further comprising a hub, the hub having a first hub portion that is engaged with the proximal portion of the first sheath, a second hub portion that is engaged with the proximal portion of the second sheath, and a third hub portion that is engaged with the proximal portion of the outer sheath, wherein the hub allows the first sheath, the second sheath, and the outer sheath to be independently manipulated.

32. The system of claim 31, wherein the third hub portion is removable and configured to allow the outer sheath to be swapped for another sheath.

33. The system of claim 31, wherein each of the first hub portion, the second hub portion and the third hub portion are configured to receive the guidewire.

34. The system of claim 1, further comprising a deflection mechanism attached to the first sheath at a location between the first distal protection filter and the second distal protection filter after deployment of both distal protection filters.

35. The system of claim 34, wherein the deflection mechanism is an inflatable balloon.

36. The system of claim 34, wherein the deflection mechanism is a flat shield.

37. The system of claim 1 wherein first and second distal protection filters both extend away from the plane in a same direction that is substantially orthogonal to the plane so that both protection filters are entirely positioned on the same side of the plane running along and parallel to the longitudinal axis.

38. The system of claim 1 wherein the first distal protection filter is directly attached to the distal portion of the first sheath and the second distal protection filter is directly attached to the distal portion of the second sheath.

* * * * *